US012460202B2

(12) United States Patent
Zhang et al.

(10) Patent No.: US 12,460,202 B2
(45) Date of Patent: Nov. 4, 2025

(54) COMPOSITIONS AND METHODS FOR PREPARING NUCLEIC ACID LIBRARIES

(71) Applicant: GUANGZHOU BURNING ROCK DX CO., LTD., Guangdong (CN)

(72) Inventors: Zhihong Zhang, Guangzhou (CN); Tao Zheng, Guangzhou (CN); Bingsi Li, Guangzhou (CN); Wanglong Deng, Guangzhou (CN); Yusheng Han, Guangzhou (CN)

(73) Assignee: GUANGZHOU BURNING ROCK DX CO., LTD., Guangzhou (CN)

( * ) Notice: Subject to any disclaimer, the term of this patent is extended or adjusted under 35 U.S.C. 154(b) by 0 days.

(21) Appl. No.: 17/225,082

(22) Filed: Apr. 7, 2021

(65) Prior Publication Data

US 2021/0254051 A1 Aug. 19, 2021

Related U.S. Application Data

(63) Continuation of application No. 17/044,723, filed as application No. PCT/CN2019/081059 on Apr. 2, 2019, which is a continuation of application No. PCT/CN2018/081748, filed on Apr. 3, 2018.

(51) Int. Cl.
*C12N 15/10* (2006.01)

(52) U.S. Cl.
CPC ................................ *C12N 15/1093* (2013.01)

(58) Field of Classification Search
CPC ............................ C12N 15/10; C12N 15/1093
See application file for complete search history.

(56) References Cited

U.S. PATENT DOCUMENTS

| | | | | |
|---|---|---|---|---|
| 5,130,238 | A | 7/1992 | Malek et al. | |
| 5,399,491 | A | 3/1995 | Kacian et al. | |
| 5,455,166 | A | 10/1995 | Walker | |
| 5,494,810 | A | 2/1996 | Barany et al. | |
| 5,648,211 | A | 7/1997 | Fraiser et al. | |
| 5,705,365 | A | 1/1998 | Ryder et al. | |
| 5,710,029 | A | 1/1998 | Ryder et al. | |
| 5,830,711 | A | 11/1998 | Barany et al. | |
| 5,854,033 | A | 12/1998 | Lizardi | |
| 5,888,779 | A | 3/1999 | Kacian et al. | |
| 6,210,891 | B1 | 4/2001 | Nyren et al. | |
| 6,410,278 | B1 | 6/2002 | Notomi et al. | |
| 7,033,764 | B2 | 4/2006 | Korlach et al. | |
| 7,094,536 | B2 | 8/2006 | Kurn | |
| 7,416,844 | B2 | 8/2008 | Korlach et al. | |
| 9,115,386 | B2 | 8/2015 | Rao et al. | |
| 9,388,465 | B2 * | 7/2016 | Hindson | C12Q 1/6806 |
| 9,822,394 | B2 | 11/2017 | Ost et al. | |
| 11,326,202 | B2 * | 5/2022 | Zheng | C12Q 1/6858 |
| 2004/0058378 | A1 | 3/2004 | Kong et al. | |
| 2010/0075384 | A1 | 3/2010 | Kong et al. | |
| 2012/0071331 | A1 | 3/2012 | Casbon et al. | |
| 2013/0231253 | A1 * | 9/2013 | Amorese | C12N 15/1072 506/2 |
| 2014/0121116 | A1 | 5/2014 | Richards et al. | |
| 2015/0087027 | A1 * | 3/2015 | Makarov | C12Q 1/6855 435/91.3 |
| 2015/0087535 | A1 | 3/2015 | Patel | |
| 2015/0299781 | A1 | 10/2015 | Ost | |
| 2016/0251700 | A1 | 9/2016 | Ost et al. | |
| 2016/0304954 | A1 | 10/2016 | Lin et al. | |
| 2017/0145492 | A1 * | 5/2017 | Pham | C12N 15/1072 |
| 2017/0362636 | A1 * | 12/2017 | Rajagopal | C12Q 1/686 |
| 2018/0223321 | A1 | 8/2018 | Makarov et al. | |

FOREIGN PATENT DOCUMENTS

| | | | |
|---|---|---|---|
| CN | 104264231 | A | 1/2015 |
| CN | 106192021 | A | 12/2016 |
| CN | 106497920 | A | 3/2017 |
| JP | 2015-510766 | A | 4/2015 |
| WO | WO 2013/112923 | A1 | 8/2013 |
| WO | WO 2013/138536 | A1 | 9/2013 |
| WO | WO 2015/124955 | A1 | 8/2015 |
| WO | WO 2015/134552 | A1 | 9/2015 |
| WO | WO 2016/077602 | A1 | 5/2016 |

OTHER PUBLICATIONS

Li et al., Towards Clinical Molecular Diagnosis of Inherited Cardiac Conditions: A Comparison of Bench-Top Genome DNA Sequencers, PLoS One, 2013, 8(7), 1-10. (Year: 2013).*

Qiagen, Qiagen OneStep RT-PCR Handbook, 2012, 1-44. (Year: 2012).*

Shanker et al., Evaluation of Commercially Available RNA Amplification Kits for RNA Sequencing Using Very Low Input Amounts of Total RNA, Journal of Biomolecular Techniques, 2015, 26, 4-18. (Year: 2015).*

*Ariad Pharmaceuticals, Inc.* v. *Eli Lilly and Co.*, 2010, 598 F.3d 1336, 1351-53 (Fed. Cir. 2010). (Year: 2010).*

Green et al., Inverse Polymerase Chain Reaction (PCR), Cold Spring Harbor Protocols, 2019, 170-174. (Year: 2019).*

Grisedale et al., Linear Amplification of Target Prior to PCR for Improved Low Template DNA Results, BioTechniques, 2014, 56(3), 145-147. (Year: 2014).*

Bhilare et al., Template Independent Synthesis of Nucleic Acid Libraries, Journal of DNA and RNA Research, 2017, 1-9; DOI :10.14302/issn.2575-7881.jdrr-17-1749. (Year: 2017).*

(Continued)

*Primary Examiner* — Amy M Bunker

(74) *Attorney, Agent, or Firm* — Jones Day

(57) ABSTRACT

In various aspects, the present disclosure provides methods, compositions, reaction mixtures, kits, and systems for preparing nucleic acid libraries, such as for polynucleotide sequencing. In some embodiments, preparation methods comprise tailing reactions, ligation reactions for attaching an adapter, and an amplification reaction between ligation reactions.

14 Claims, 13 Drawing Sheets

Specification includes a Sequence Listing.

(56) References Cited

OTHER PUBLICATIONS

Bhilare et al., Supplementary Table, Template Independent Synthesis of Nucleic Acid Libraries, Journal of DNA and RNA Research, 2017 1-3; DOI :10.14302/issn.2575-7881.jdrr-17-1749. (Year: 2017).*
International Search Report and Written Opinion of International Patent Application No. PCT/CN2018/081748 mailed on Jan. 9, 2019.
International Search Report and Written Opinion of International Patent Application No. PCT/CN2019/081059 mailed on Jul. 5, 2019.
Wharam et al., "Specific detection of DNA and RNA targets using a novel isothermal nucleic acid amplification assay based on the formation of a three-way junction structure," Nucleic Acids Res., 29:e54 (2001).
Oritani et al., "Identification Of Stromal Cell Products That Interact With Pre-B Cells," *The Journal of Cell Biology*, 134(3):771-782 (1996).
Bhilare et al., "Template Independent Synthesis of Nucleic Acid Libraries," *Journal of DNA and RNA Research*, 1(2):1-9 (2017).
Liang et al., "Ultrasensitive detection of circulating tumour DNA via deep methylation sequencing aided by machine learning," Nature Biomedical Engineering, Available at: https://doi.org/10.1038/s41551-021-00746-5, 1-34 (2021).

* cited by examiner

SEQUENCE LISTING

```
<160> NUMBER OF SEQ ID NOS: 23

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ccctcctc                                                                8


<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tttttttttt tt                                                          12


<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```

aaaaaaaaaa aa 12

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
agatcggaag agcacacgtc tgaactccag tcac 34

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
gtgactggag ttcagacgtg tgctcttccg atctrrrrrr rr 42

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
agatcggaag agcgtcgtgt agggaaagag tgt 33

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
acactctttc cctacacgac gctcttccga tctttttttt ttttt 45

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
acactctttc cctacacgac gctcttccga tct 33

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
agatcggaag agcacacgtc tgaactccag tcac 34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
agatcggaag agcacacgtc tgaactccag tcac 34

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
acactctttc cctacacgac gctcttccga tct 33

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
acactctttc cctacacgac gctcttccga tcttttttttt ttttt 45

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
ccctcctcag atcggaagag cacacgtctg aactccagtc ac 42

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
aaaaaaaaaa aaagatcgga agagcgtcgt gtagggaaag agtgt 45

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
gtgactggag ttcagacgtg tgctcttccg atctrrrrrr rr 42

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtgactggag ttcagacgtg tgctcttccg atc 33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
acactctttc cctacacgac gctcttccga tct 33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gtgactggag ttcagacgtg tgctcttccg atc 33

<210> SEQ ID NO 19
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aatgatacgg cgaccaccga gatctacacg ttagttcaca ctctttccct acacgacg 58

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
caagcagaag acggcatacg agatgtgatg ccgtgactgg agttcagacg tg 52

<210> SEQ ID NO 21
<211> LENGTH: 16
<212> TYPE: DNA
<213> ORGANISM: Unknown
<220> FEATURE:
<223> OTHER INFORMATION: Description of Unknown: EGFR sequence

<400> SEQUENCE: 21
aggaattaag agaagc 16

```
<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

agtcgtgact ggagttcaga cgtgtgctct tccgatctrr rrrrrr                46


<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(40)
<223> OTHER INFORMATION: a, c, t, or g

<400> SEQUENCE: 23

acactctttc cctacacgac gctcttccga tctnnnnnnn                        40
```

COMPOSITIONS AND METHODS FOR PREPARING NUCLEIC ACID LIBRARIES

This application is a continuation of U.S. application Ser. No. 17/044,723, filed Oct. 1, 2020, which is the U.S. National Stage Application under 35 U.S.C. § 371 of International Patent Application No. of PCT/CN2019/081059, filed Apr. 2, 2019, which claims the benefit of priority of International Patent Application No. PCT/CN2018/081748, filed Apr. 3, 2018, the entire disclosures of each of which are herein incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Nov. 18, 2020, is named 14499-004-999 Sequence Listing. TXT and is 5,759 bytes in size.

BACKGROUND

Identifying and analyzing complex nucleic acid populations is an active field of development with multiple applications. Such analyses have been greatly facilitated by large-scale parallel nucleic acid sequencing (also referred to as "high-throughput sequencing" or "next generation sequencing" (NGS)). Due to challenges such as small sample input and errors at various stages in manipulation, it remains difficult to detect nucleic acid species that are present in relatively low abundance. Such challenges can arise in situations like testing for possible contaminants (e.g., in food or water), detecting the presence of a particular bacteria in a complex population (e.g., in environmental testing), and detecting presence of nucleic acids associated with disease (e.g. infection, or cancer), particularly at early stages.

SUMMARY

In view of the foregoing, there is a need for improved methods of preparing nucleic acid libraries. Compositions and methods disclosed herein address this need, and provide additional advantages as well.

In one aspect, the present disclosure provides methods for preparing a polynucleotide library. In some embodiments, the methods comprise (a) in a first tailing reaction, adding a first tail to each of a plurality of target polynucleotides by template-independent polymerization, wherein the first tailing reaction comprises a first adapter comprising an overhang that hybridizes to the first tail; (b) in a first ligation reaction, ligating a strand of the first adapter to the first tail; (c) amplifying target polynucleotides comprising the strand of the first adapter by extending a first primer hybridized to the strand of the first adapter; (d) in a second tailing reaction, adding a second tail to each of a plurality of the amplified target polynucleotides by template-independent polymerization, wherein the second tailing reaction comprises a second adapter comprising an overhang that hybridizes to the second tail; and (e) in a second ligation reaction, ligating a strand of the second adapter to the second tail. In some embodiments, the method comprises one or more of: (a) fragmenting polynucleotides to produce the target polynucleotides; (b) dephosphorylation of one or both ends of the target polynucleotides; and (c) denaturing double-stranded polynucleotides to single-stranded polynucleotides to produce the target polynucleotides. In some embodiments, the plurality of target polynucleotides comprises single-stranded DNA. In some embodiments, the target polynucleotides comprise cell-free polynucleotides, or amplification products thereof. In some embodiments, the target polynucleotides comprise single-stranded cell-free DNA (cfDNA). In some embodiments, the amount of target polynucleotides in the first tailing reaction is about 0.1-500 ng, 1-100 ng, or 5-50 ng. In some embodiments, the target polynucleotides have an average length of about 50 to 600 nucleotides. In some embodiments, the target polynucleotides are treated prior to the first ligation reaction to differentially modify methylated cytosines or unmethylated cytosines, such as by treating the target polynucleotides with bisulfite. In some embodiments, the template-independent polymerization is catalyzed by a polymerase, such as a terminal deoxynucleotidyl transferase (TdT). In some embodiments, the first tail comprises a sequence that is different from the second tail. In some embodiments, the first tail and the second tail comprise the same sequence. In some embodiments, the first tail, the second tail, or both consist of one or two types of nucleotides. In some embodiments, the first tail, the second tail, or both are selected from the group consisting of poly-A, poly-C, and poly-C/T. In some embodiments, at least one of the tails consists of two types of nucleotides polymerized from a pool of the two types of nucleotides, wherein the two types of nucleotides in the pool are present in same or different amounts. In some embodiments, the two types of nucleotides in the pool are in a ratio of about 9:1, 5:1, 3:1, or 1:1. In some embodiments, the first adapter and the second adapter comprise double-stranded regions that are different in polynucleotide sequence. In some embodiments, the amplifying comprises linear amplification. In some embodiments, the overhang of the first and/or second adapter is a 3'-overhang. In some embodiments, the overhang of the first and/or second adapter is 6 to 12 nucleotides in length. In some embodiments, (i) the first tailing reaction and the first ligation reaction occur in the same reaction mixture, and/or (ii) the second tailing reaction and the second ligation reaction occur in the same reaction mixture.

In some embodiments, the method further comprises amplifying target polynucleotides comprising the strand of the second adapter by extending a second primer hybridized to the strand of the second adapter. In some embodiments, the sequence of the first primer that hybridizes with the strand of the first adapter is different from the sequence of the second primer that hybridizes with the second adapter. In some embodiments, amplification with the primer hybridized to the strand of the second adapter is an exponential amplification. In some embodiments, the method further comprises an amplification reaction with a third primer and a fourth primer, wherein (i) the third primer hybridizes to a complement of at least a portion of the first primer, and (ii) the fourth primer hybridizes to a complement of at least a portion of the second primer. In some embodiments, the hybridizable sequence of the third primer is different from the hybridizable sequence of the first primer, and/or the hybridizable sequence of the fourth primer is different from the hybridizable sequence of the second primer. In some embodiments, the sequences of the third primer and the fourth primer are different. In some embodiments, the third primer, the fourth primer, or both comprise an index sequence that identifies a sample source of the target polynucleotides. In some embodiments, the method further comprises sequencing amplification products of the amplification comprising the second primer. In some embodiments, the method further comprises sequencing amplification products of the amplification comprising the third and fourth primer. In some embodiments, the method further comprises grouping sequencing reads according to the index sequence. In some embodiments, sequencing comprises detecting a sequence variant or a difference in nucleotide methylation, relative to a reference sequence.

In one aspect, the present disclosure provides compositions for use in one or more methods described herein.

In one aspect, the present disclosure provides a polynucleotide produced according to any of the methods described herein.

In one aspect, the present disclosure provides kits for preparing a polynucleotide library. In some embodiments, the kit comprises: (a) a template-independent polymerase; (b) a first pool of nucleotides that can be polymerized by the template-independent polymerase; (c) a second pool of nucleotides that can be polymerized by the template-independent polymerase; (d) a first adapter comprising an overhang that is hybridizable to tails formed by polymerizing the first pool of polynucleotides; and (e) a second adapter comprising an overhang that is hybridizable to tails formed by polymerizing the second pool of polynucleotides, wherein the second adapter comprises a different sequence than the first adapter. In some embodiments, the template-independent polymerase is a terminal deoxynucleotidyl transferase (TdT). In some embodiments, at least one of the first pool and the second pool contains at least one type of nucleotide not present in the other pool. In some embodiments, the first pool and the second pool comprise the same one or more types of nucleotides. In some embodiments, the first pool, the second pool, or both consist of one or two types of nucleotides. In some embodiments, the first pool, the second pool, or both are selected from the group consisting of (i) a pool of dATP, (ii) a pool of dCTP, and (iii) a pool of dCTP and dTTP. In some embodiments, at least one of the first pool and the second pool consists of two types of nucleotides that are present in same or different amounts. In some embodiments, the two types of nucleotides in the pool are in a ratio of about 9:1, 5:1, 3:1, or 1:1. In some embodiments, the first adapter and the second adapter comprise double-stranded regions that are different in polynucleotide sequence. In some embodiments, the overhang of the first and/or second adapter is a 3'-overhang. In some embodiments, the overhang of the first and/or second adapter is 6 to 12 nucleotides in length. In some embodiments, the kit further comprises a first primer that is hybridizable to a strand of the first adapter under conditions for a primer extension reaction. In some embodiments, the kit further comprises a second primer that is hybridizable to a strand of the second adapter under conditions for a primer extension reaction. In some embodiments, the sequence of the first primer that is hybridizable to the strand of the first adapter is different from the sequence of the second primer that is hybridizable to the second adapter. In some embodiments, the kit further comprises a third primer and a fourth primer, wherein (i) the third primer is hybridizable to a complement of at least a portion of the first primer under conditions for a primer extension reaction, and (ii) the fourth primer is hybridizable to a complement of at least a portion of the second primer under conditions for a primer extension reaction. In some embodiments, the hybridizable sequence of the third primer is different from the hybridizable sequence of the first primer, and/or the hybridizable sequence of the fourth primer is different from the hybridizable sequence of the second primer. In some embodiments, the hybridizable sequence of the third primer hybridizes 5' with respect to the hybridizable sequence of the first primer, and/or the hybridizable sequence of the fourth primer hybridizes 5' with respect to the hybridizable sequence of the second primer. In some embodiments, the sequences of the third primer and fourth primer are different. In some embodiments, the third primer, the fourth primer, or both comprise an index sequence that identifies a sample source of the target polynucleotides.

In some embodiments of methods of the invention for preparing a polynucleotide library, the methods comprise (a) in a first tailing reaction, adding a first tail to each of a plurality of target polynucleotides by template-independent polymerization, wherein the first tailing reaction comprises a first adapter comprising an overhang that hybridizes to the first tail; (b) in a first ligation reaction, ligating a strand of the first adapter to the first tail; (c) amplifying target polynucleotides comprising the strand of the first adapter by extending a first primer hybridized to the strand of the first adapter; and (d) in a second ligation reaction, ligating a strand of a second adapter to the amplified target polynucleotides. In some embodiments, the second ligation reaction comprises, in a second tailing reaction, adding a second tail to each of a plurality of the amplified target polynucleotides by template-independent polymerization. In some embodiments, the second tailing reaction comprises a second adapter comprising an overhang that hybridizes to the second tail. In some embodiments, in the second ligation reaction, ligating a strand of the second adapter to the second tail. In some embodiments, the second ligation reaction comprises a second adapter comprising an overhang that hybridizes to the amplified target polynucleotides.

In some embodiments, the method comprises one or more of: (a) fragmenting polynucleotides to produce the target polynucleotides; (b) dephosphorylation of one or both ends of the target polynucleotides; and (c) denaturing double-stranded polynucleotides to single-stranded polynucleotides to produce the target polynucleotides. In some embodiments, the plurality of target polynucleotides comprises single-stranded DNA. In some embodiments, the target polynucleotides comprise cell-free polynucleotides, or amplification products thereof. In some embodiments, the target polynucleotides comprise single-stranded cell-free DNA (cfDNA). In some embodiments, the amount of target polynucleotides in the first tailing reaction is about 0.1-500 ng, 1-100 ng, or 5-50 ng. In some embodiments, the target polynucleotides have an average length of about 50 to 600 nucleotides. In some embodiments, the target polynucleotides are treated prior to step (b) to differentially modify methylated cytosines or unmethylated cytosines. In some embodiments, the differentially modifying comprises treating the target polynucleotides with bisulfite. In some embodiments, the template-independent polymerization is catalyzed by a polymerase. In some embodiments, the polymerase is a terminal deoxynucleotidyl transferase (TdT). In some embodiments, the first tail comprises a sequence that is different from the second tail. In some embodiments, the first tail and the second tail comprise the same sequence. In some embodiments, the first tail, the second tail, or both consist of one or two types of nucleotides. In some embodiments, the first tail, the second tail, or both are selected from the group consisting of poly-A, poly-C, and poly-C/T. In some embodiments, at least one of the tails consists of two types of nucleotides polymerized from a pool of the two types of nucleotides, wherein the two types of nucleotides in the pool are present in same or different amounts. In some embodiments, the two types of nucleotides in the pool are in a ratio of about 9:1, 7:1, 5:1, 3:1, or 1:1. In some embodiments, the second tailing reaction is omitted. In some embodiments, the first adapter and the second adapter comprise double-stranded regions that are different in polynucleotide sequence. In some embodiments, the amplifying comprises linear amplification. In some embodiments, the overhang of the first and/or second adapter is a 3'-overhang. In some embodiments, the first and/or second adapter have both a 3'-overhang and a 5'-overhang. In some embodiments, the 3'-overhang of the first and/or second adapter is 6 to 12 nucleotides in length. In some embodiments, the 5'-overhang of the first and/or second adapter is 2 to 6 nucleotides in length. In some embodiments, (i) the first tailing reaction and the first ligation reaction occur in the same reaction mixture, and/or (ii) the second tailing reaction and the second ligation reaction occur in the same reaction mixture.

In some embodiments, the method further comprises amplifying target polynucleotides comprising the strand of the second adapter by extending a second primer hybridized to the strand of the second adapter. In some embodiments, the sequence of the first primer that hybridizes with the strand of the first adapter is different from the sequence of the second primer that hybridizes with the second adapter. In some embodiments, amplification with the primer hybridized to the strand of the second adapter is an exponential amplification. In some embodiments, the method further comprises an amplification reaction with a third primer and a fourth primer, wherein (i) the third primer hybridizes to a complement of at least a portion of the first primer, and (ii) the fourth primer hybridizes to a complement of at least a portion of the second primer. In some embodiments, the hybridizable sequence of the third primer is different from the hybridizable sequence of the first primer, and/or the hybridizable sequence of the fourth primer is different from the hybridizable sequence of the second primer. In some embodiments, the sequences of the third primer and the fourth primer are different. In some embodiments, the third primer, the fourth primer, or both comprise an index sequence that identifies a sample source of the target polynucleotides. In some embodiments, the method further comprises sequencing amplification products of the amplification comprising the second primer. In some embodiments, the method further comprises sequencing amplification products of the amplification comprising the third and fourth primer. In some embodiments, the method further comprises grouping sequencing reads according to the index sequence.

In one aspect, the present disclosure provides compositions for use in one or more methods described herein.

In one aspect, the present disclosure provides a polynucleotide produced according to any of the methods described herein.

In one aspect, the present disclosure provides kits for preparing a polynucleotide library. In some embodiments, the kit comprises (a) a template-independent polymerase; (b) a first pool of nucleotides that can be polymerized by the template-independent polymerase; (c) a second pool of nucleotides that can be polymerized by the template-independent polymerase; (d) a first adapter comprising an overhang that is hybridizable to tails formed by polymerizing the first pool of polynucleotides; and (e) a second adapter comprising an overhang that is hybridizable to the amplified target polynucleotides. In some embodiments, the template-independent polymerase is a terminal deoxynucleotidyl transferase (TdT). In some embodiments, at least one of the first pool and the second pool contains at least one type of nucleotide not present in the other pool. In some embodiments, the first pool and the second pool comprise the same one or more types of nucleotides. In some embodiments, the first pool, the second pool, or both consist of one or two types of nucleotides. In some embodiments, the first pool, the second pool, or both are selected from the group consisting of (i) a pool of dATP, (ii) a pool of dCTP, and (iii) a pool of dCTP and dTTP. In some embodiments, at least one of the first pool and the second pool consists of two types of nucleotides that are present in same or different amounts. In some embodiments, the two types of nucleotides in the pool are in a ratio of about 9:1, 7:1, 5:1, 3:1, or 1:1. In some embodiments, the first adapter and the second adapter comprise double-stranded regions that are different in polynucleotide sequence. In some embodiments, the overhang of the first and/or second adapter is a 3'-overhang. In some embodiments, the first and/or second adapter have both a 3'-overhang and a 5'-overhang. In some embodiments, the 3'-overhang of the first and/or second adapter is 6 to 12 nucleotides in length. In some embodiments, the 5'-overhang of the first and/or second adapter is 2 to 6 nucleotides in length. In some embodiments, the kit further comprises a first primer that is hybridizable to a strand of the first adapter under conditions for a primer extension reaction. In some embodiments, the kit further comprises a second primer that is hybridizable to a strand of the second adapter under conditions for a primer extension reaction. In some embodiments, the sequence of the first primer that is hybridizable to the strand of the first adapter is different from the sequence of the second primer that is hybridizable to the second adapter. In some embodiments, the kit further comprises a third primer and a fourth primer, wherein (i) the third primer is hybridizable to a complement of at least a portion of the first primer under conditions for a primer extension reaction, and (ii) the fourth primer is hybridizable to a complement of at least a portion of the second primer under conditions for a primer extension reaction. In some embodiments, the hybridizable sequence of the third primer is different from the hybridizable sequence of the first primer, and/or the hybridizable sequence of the fourth primer is different from the hybridizable sequence of the second primer. In some embodiments, the hybridizable sequence of the third primer hybridizes 5' with respect to the hybridizable sequence of the first primer, and/or the hybridizable sequence of the fourth primer hybridizes 5' with respect to the hybridizable sequence of the second primer. In some embodiments, the sequences of the third primer and fourth primer are different. In some embodiments, the third primer, the fourth primer, or both comprise an index sequence that identifies a sample source of the target polynucleotides.

DETAILED DESCRIPTION

Figure 1:
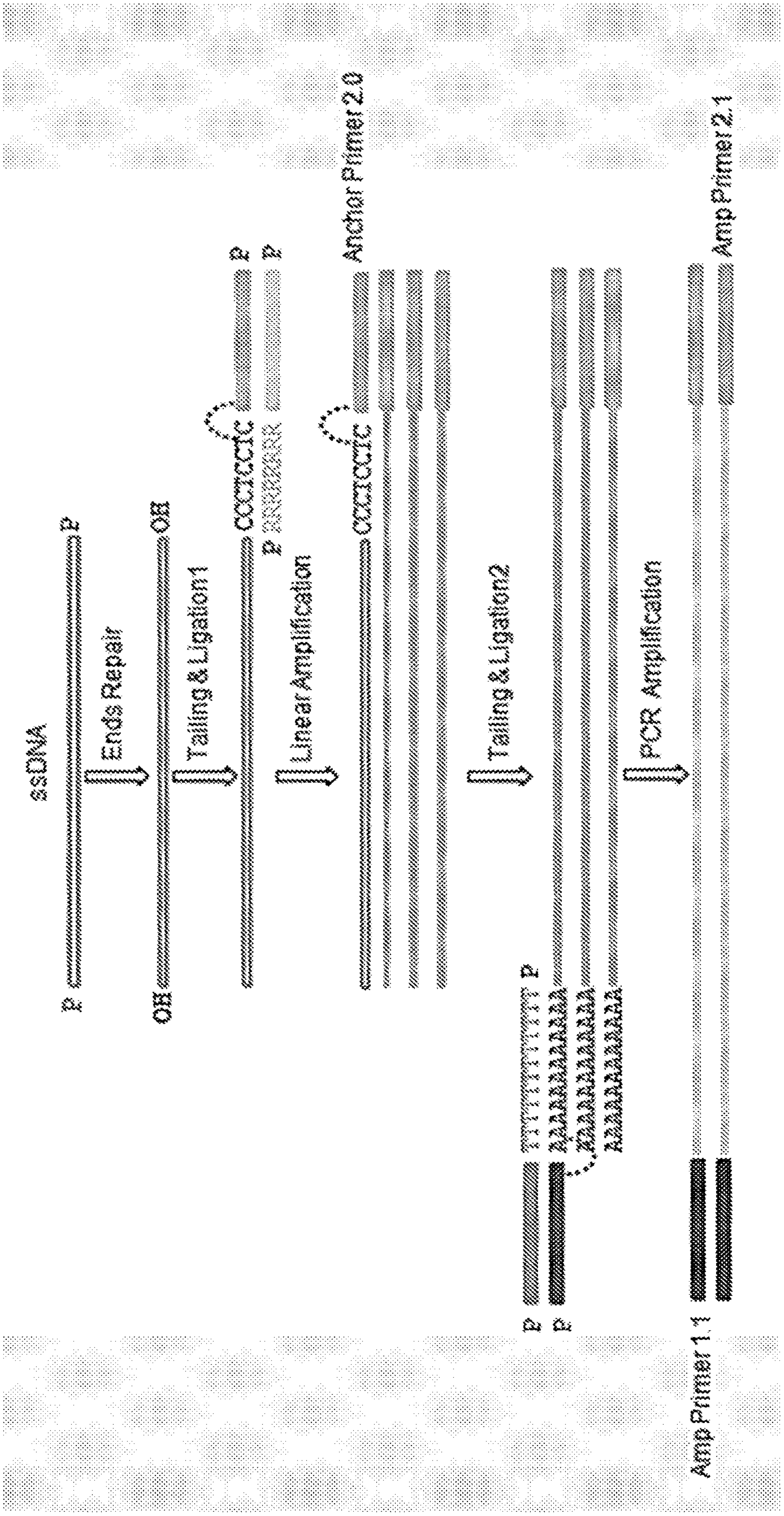
FIG. 1 illustrates an example library preparation method, in accordance with an embodiment. The illustration includes sequences CCCTCCTC (SEQ ID NO: 1), TTTTTTTTTTTT (SEQ ID NO: 2), and AAAAAAAAAAAA (SEQ ID NO: 3).

The practice of certain steps of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R.I. Freshney, ed. (2010)).

As used in the specification and claims, the singular form “a”, “an” and “the” include plural references unless the context clearly dictates otherwise.

The term “about” or “approximately” means within an acceptable error range for the particular value as determined by one of ordinary skill in the art, which will depend in part on how the value is measured or determined, i.e., the limitations of the measurement system. For example, “about” can mean within one or more than one standard deviation, per the practice in the art. Alternatively, “about” can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

The terms “polynucleotide”, “nucleotide”, “nucleic acid,” and “oligonucleotide” are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, primers, and adapters. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In general, the terms “cell-free,” “circulating,” and “extracellular” as applied to polynucleotides (e.g. “cell-free DNA” and “cell-free RNA”) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or “free” from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

As used herein, a “subject” can be a mammal such as a non-primate (e.g., cows, pigs, horses, cats, dogs, rats, etc.) or a primate (e.g., monkey or human). In some embodiments, the subject is a human. In some embodiments, the subject is a mammal (e.g., a human) having or potentially having a disease, disorder, or condition, examples of which are described herein. In some embodiments, the subject is a mammal (e.g., a human) at risk of developing a disease, disorder, or condition, examples of which are described herein.

The terms “amplify,” “amplifies,” “amplified,” and “amplification,” as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation.

“Hybridization” refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is perfectly complementary to a first sequence, or is polymerized by a polymerase using the first sequence as template, is referred to as the “complement” of the first sequence. The term “hybridizable” as applied to a polynucleotide refers to the ability of the polynucleotide to form a complex that is stabilized via hydrogen bonding between the bases of the nucleotide residues in a hybridization reaction. In some embodiments, a hybridizable sequence of nucleotides is at least about 50%, 60%, 70%, 75%, 80%, 85%, 90%, 95%, or 100% complementary to the sequence to which it hybridizes. In some embodiments, a hybridizable sequence is one that hybridizes to one or more target sequences as part of, and under the conditions of, a step in a multi-step process (e.g., a ligation reaction, or an amplification reaction).

"Complementarity" refers to the ability of a nucleic acid to form hydrogen bond(s) with another nucleic acid sequence by either traditional Watson-Crick base pairing or other non-traditional types. A percent complementarity indicates the percentage of residues in a first nucleic acid sequence which can form hydrogen bonds (e.g., Watson-Crick base pairing) with a second nucleic acid sequence (e.g., 5, 6, 7, 8, 9, or 10 out of 10 being 50%, 60%, 70%, 80%, 90%, and 100% complementary, respectively). "Perfectly complementary" means that all the contiguous residues of a first nucleic acid sequence will hydrogen bond with the same number of contiguous residues in a second nucleic acid sequence. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, the term "sequence variant" refers to any variation in sequence relative to one or more reference sequences. Typically, the sequence variant occurs with a lower frequency than the reference sequence for a given population of individuals for which the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including but not limited to a translocation or fusion gene.

In one aspect, the present disclosure provides methods for preparing a polynucleotide library. In some embodiments, the methods comprise (a) in a first tailing reaction, adding a first tail to each of a plurality of target polynucleotides by template-independent polymerization, wherein the first tailing reaction comprises a first adapter comprising an overhang that hybridizes to the first tail; (b) in a first ligation reaction, ligating a strand of the first adapter to the first tail; (c) amplifying target polynucleotides comprising the strand of the first adapter by extending a first primer hybridized to the strand of the first adapter; (d) in a second tailing reaction, adding a second tail to each of a plurality of the amplified target polynucleotides by template-independent polymerization, wherein the second tailing reaction comprises a second adapter comprising an overhang that hybridizes to the second tail; and (e) in a second ligation reaction, ligating a strand of the second adapter to the second tail.

In one aspect, the present disclosure provides methods for preparing a polynucleotide library. In some embodiments, the methods comprise (a) in a first tailing reaction, adding a first tail to each of a plurality of target polynucleotides by template-independent polymerization, wherein the first tailing reaction comprises a first adapter comprising an overhang that hybridizes to the first tail; (b) in a first ligation reaction, ligating a strand of the first adapter to the first tail; (c) amplifying target polynucleotides comprising the strand of the first adapter by extending a first primer hybridized to the strand of the first adapter; and (d) in a second ligation reaction, ligating a strand of a second adapter to the amplified target polynucleotides. In such an embodiment, the second adaptor ligation is used without a tailing reaction. Optionally in such a method, the second ligation reaction can comprise, in a second tailing reaction, adding a second tail to each of a plurality of the amplified target polynucleotides by template-independent polymerization. In one embodiment, the second tailing reaction can comprise a second adapter comprising an overhang that hybridizes to the second tail. In one embodiment, in the second ligation reaction, ligating a strand of the second adapter to the second tail. In one embodiment, the second ligation reaction comprises a second adapter comprising an overhang that hybridizes to the amplified target polynucleotides. Such an embodiment allows for subsequent ligation. In one embodiment, the second adaptor ligation can utilize a 3' overhang of random bases in the adaptor to serve as a splinter to facilitate ligation. The second adapters can be added to the 3' ends of the amplified target polynucleotides. The 3' overhang of the adapter serves as a splinter to stabilize the substrate strand and facilitate the ligation between the 3' end of the substrate strand and the 5' end of the phosphorylated opposite adapter strand.

Polynucleotides useful in methods of the present disclosure can be derived from any of a variety of sample sources. In some embodiments, the sample is an environmental sample, such as a naturally occurring or artificial atmosphere, water sample, soil sample, surface swab, or any other sample of interest. In some embodiments, polynucleotides are derived from a biological sample, such as a sample of a subject. Non-limiting examples of biological samples include tissues (e.g. skin, heart, lung, kidney, bone marrow, breast, pancreas, liver, muscle, smooth muscle, bladder, gall bladder, colon, intestine, brain, prostate, esophagus, thyroid, and tumor), bodily fluids (e.g. blood, blood fractions, serum, plasma, saliva, urine, breast milk, gastric and digestive fluid, tears, semen, vaginal fluid, interstitial fluids derived from tumorous tissue, ocular fluids, sweat, mucus, oil, glandular secretions, spinal fluid, cerebral spinal fluid, placental fluid, amniotic fluid, cord blood, cavity fluids, sputum, pus), stool, swabs or washes (e.g. nasal swab, throat swab, and nasopharyngeal wash), biopsies, and other excretions or body tissues. In some embodiments, the sample is blood, a blood fraction, plasma, serum, saliva, sputum, urine, semen, transvaginal fluid, cerebrospinal fluid, or stool. In some embodiments, the sample is blood, such as whole blood or a blood fraction (e.g. serum or plasma).

In some embodiments, polynucleotides are extracted from a sample, such as when polynucleotides to be analyzed are contained within cells or viral capsids. Where an extraction method is used, the method selected may depend, in part, on the type of sample to be processed. A variety of extraction methods are available. For example, nucleic acids can be purified by organic extraction with phenol, phenol/chloroform/isoamyl alcohol, or similar formulations, including TRIzol and TriReagent. In some embodiments, samples are treated to remove or degrade one or more components, such as protein (e.g., by proteinase K treatment) or RNA (e.g., by RNaseA treatment), and/or to preserve one or more components, such as RNA (e.g., by treatment with RNase inhibitor). When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after subsequent manipulation, such as to remove excess or unwanted reagents, reactants, or products.

In some embodiments, the methods described herein involve manipulation of cell-free polynucleotides obtained from a sample of a subject without cellular extraction (e.g. without a step for lysing cells, viruses, and/or other capsules comprising nucleic acids). In some embodiments, polynucleotides are manipulated directly in a biological sample as collected. In some embodiments, cell-free polynucleotides are separated from other components of a sample (e.g. cells and/or proteins) without treatment to release polynucleotides contained in cells that may be present in the sample. For samples comprising cells, the sample can be treated to separate cells from the sample. In some embodiments, a sample is subjected to centrifugation and the supernatant comprising the cell-free polynucleotides is separated for further processing (e.g. isolation of polynucleotides from other components, or other manipulation of the polynucleotides). In some embodiments, cell-free polynucleotides are purified away from other components of an initial sample (e.g. cells and/or proteins). A variety of procedures for isolation of polynucleotides without cellular extraction are available, such as by precipitation or non-specific binding to a substrate followed by washing the substrate to release bound polynucleotides.

The starting amount of polynucleotides isolated from a sample source (e.g., an environmental sample, or a sample from a subject) can vary, and in some cases may be small. In some embodiments, the amount of starting polynucleotides is about or less than about 1000 ng, 500 ng, 100 ng 50 ng, 25 ng, 20 ng, 15 ng, 10 ng, 5 ng, 4 ng, 3 ng, 2 ng, 1 ng, 0.5 ng, 0.1 ng, or less. In some embodiments, the amount of starting polynucleotides is in the range of about 0.1-500 ng, such as between 1-100 ng or 5-50 ng. In general, lower starting material increases the importance of recovering polynucleotides from one processing step to the next. Processes that reduce the amount of polynucleotides in a sample for participation in a subsequent reaction decrease the sensitivity with which rare polynucleotides (e.g., mutations) can be detected. In some embodiments, methods disclosed herein increase the detection sensitivity relative to prior detection methods.

In some embodiments, polynucleotides to be analyzed comprise amplification products of polynucleotides from a sample. Amplification products can be specifically amplified (e.g., by using target-specific amplification primers), or non-specifically amplified (e.g., by using a pool of non-specific amplification primers). In some embodiments, amplification templates comprise DNA and/or RNA. In some embodiments, polynucleotides to be analyzed comprise RNA that is reverse-transcribed into DNA as part of a reverse transcription (RT) reaction. In general, reverse transcription comprises extension of an oligonucleotide primer hybridized to a target RNA by an RNA-dependent DNA polymerase (also referred to as a "reverse transcriptase"), using the target RNA molecule as the template to produce a complementary DNA (cDNA). Examples of reverse transcriptases include, but are not limited to, retroviral reverse transcriptase (e.g., Moloney Murine Leukemia Virus (M-MLV), Avian Myeloblastosis Virus (AMV) or Rous Sarcoma Virus (RSV) reverse transcriptases), Superscript ITM, Superscript II™, Superscript III™, retrotransposon reverse transcriptase, hepatitis B reverse transcriptase, cauliflower mosaic virus reverse transcriptase, bacterial reverse transcriptase, and mutants, variants or derivatives thereof. In some embodiments, the reverse transcriptase is a hot-start reverse transcriptase enzyme.

In some embodiments, the polynucleotides are polynucleotides that have been subjected to fragmentation. In some embodiments, the fragments have an average length, median length, or fractional distribution of lengths (e.g., accounting for at least 50%, 60%, 70%, 80%, 90%, or more) that is less than a predefined length or within a predefined range of lengths. In some embodiments, the predefined length is about or less than about 1500, 1000, 800, 600, 500, 300, 200, 100, or 50 nucleotides in length. In some embodiments, the predefined range of lengths is a range between 10-1000, 10-800, 10-700, 50-600, 100-600, or 150-400 nucleotides in length. In some embodiments, the fragmented polynucleotides have an average size within a pre-defined range (e.g. an average or median length from about 10 to about 1,000 nucleotides in length, such as between 10-800, 10-700, 50-600, 100-600, or 150-400 nucleotides; or an average or medium length of less than 1500, 1000, 750, 500, 400, 300, 250, 100, 50, or fewer nucleotides in length).

In some embodiments, fragmenting the polynucleotides comprises mechanical fragmentation, chemical fragmentation, and/or heating. In some embodiments, the fragmentation is accomplished mechanically comprising subjecting sample polynucleotides to acoustic sonication. In some embodiments, the fragmentation comprises treating the sample polynucleotides with one or more enzymes under conditions suitable for the one or more enzymes to generate nucleic acid breaks (e.g., double-stranded breaks). Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of Mg++ and in the presence of Mn++. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. Fragmented polynucleotides may be subjected to a step of size selecting the fragments, such as column purification or isolation from an agarose gel.

In some embodiments, polynucleotides are treated to prepare the 5' ends and/or the 3' ends for subsequent steps, such as extension or ligation steps. Preparation of polynucleotide ends can be particularly helpful following fragmentation procedures. Preparation of polynucleotide ends is often referred to as end "polishing" or "repair." In some embodiments, polynucleotide ends are repaired to generate blunt-end or single-stranded fragments with 5' phosphorylated ends (e.g., using dNTP, T4 DNA polymerase, Klenow large fragment, T4 Polynucleotide Kinase, and ATP). In some embodiments, end repair comprises adding an adenine to the 3' ends to generate a 3'-A overhang (e.g., using dATP, Klenow fragment (3'-5' exo-) or Taq polymerase). In some embodiments, one or both polynucleotide ends are dephosphorylated, such as by treatment with a phosphatase.

In some embodiments, the methods comprise a first tailing reaction, in which a first tail is added to each of a plurality of target polynucleotides by template-independent polymerization. In some embodiments, the target polynucleotides are single-stranded. The target polynucleotides may be naturally single-stranded, or treated to be single-stranded if not already so. For example, target RNA can be reverse-transcribed to form DNA-RNA hybrid molecules, which can then be treated with RNaseH or heat-denatured in the presence of RNase A to degrade the RNA and yield single-stranded cDNA. As a further example, double-stranded DNA can be heat-denatured (e.g., by incubation at about 95° C.), optionally followed by rapid cooling (e.g., incubation on ice). In some embodiments, the target polynucleotides comprise single-stranded DNA. In some embodiments, the target polynucleotides comprise single-stranded cfDNA.

In general, the "tail" produced by template-independent polymerization refers to the newly-synthesized string of nucleotides polymerized to the end of a target polynucleotide subjected to the polymerization reaction. The length and nucleotide sequence of the tail will depend, in part, on the type of nucleotides from which the tail is polymerized (e.g., 1, 2, 3, or 4 of A, T, G, and C), the duration of the reaction, the polymerase used, and the presence of other reagents (e.g. an adapter comprising an overhang that hybridizes to the first tail during the polymerization reaction). In some embodiments, the tail is polymerized only to the 3' end of one or more target polynucleotides.

In some embodiments, a tail is polymerized from a pool consisting of four types of DNA bases (A, T, G, and C), such that the resulting tail has a chance of comprising any or all four of the bases. In some embodiments, a tail is polymerized from a pool consisting of any three of the bases A, T, G, and C, such that the resulting tail has a chance of comprising any or all of the three selected bases. In some embodiments, a tail is polymerized from a pool consisting of any two types of the bases A, T, G, and C, such as C/T or A/G, such that the resulting tail has a chance of comprising either or both of the two selected bases. In some embodiments, a tail is polymerized from a pool consisting of one type of base selected from A, T, G, and C, such that the resulting tail consists of bases of the selected type. In some embodiments, the pool consists of thymine bases (yielding a poly-T tail) or cytosine bases (yielding a poly-C tail). Typically, the bases are in a triphosphate form (e.g. dATP, dTTP, dGTP, and/or dCTP). When there is more than one type of base in the pool, constitution of the tail can be modulated by adjusting the ratio of the types of bases in the pool. In some embodiments, all types of bases in the pool are present in approximately equal amounts, such that the ratio of any one type to any other type is about 1:1. In some embodiments, the ratio of one type of base to another in the pool is about or more than about 2:1, 3:1, 4:1, 5:1, 6:1, 7:1, 8:1, 9:1, 10:1, 15:1, or higher. In some embodiments, the ratio of one type of base to another in the pool is about or more than about 3:1, 5:1, or 9:1. In some embodiments, the ratio is about or more than about 9:1. When more than one type of nucleotide is present in the pool, the sequence of the tail can be represented as a degenerate sequence of letters representing the members of the pool. For example, "RRR" refers to a sequence of three purines and represents the sequences AAA, AAG, AGA, GAA, AGG, GAG, GGA, and GGG; "YYY" refers to a sequence of three pyrimidines and represents the sequences TTT, TTC, TCT, CTT, TCC, CCT, CTC, and CCC. In such circumstances, the tail on one molecule may or may not be the same as another. However, the set of possible sequences and their relative likelihoods within a resulting pool of tailed polynucleotides can be modulated based on the types of nucleotides in the pool and their relative amounts. In embodiments comprising more than one tailing reaction, the conditions of each reaction can be selected to produce tails that are the same or different, such as in terms of length, types of nucleotides included, and/or relative amounts of nucleotides if more than one is present in the pool. In some embodiments, the method comprises two tailing reactions and the tails are the same. In some embodiments, the method comprises two tailing reactions and the tails are different.

In some embodiments, one or more steps comprise polynucleotide extension by a polymerase. Example polynucleotide extension reactions include reverse transcription, tailing, and amplification. A variety of polymerases are available and can be suitably selected for the appropriate type of polynucleotide extension reaction. In some embodiments, the polynucleotide extension reaction is a tailing reaction, such as a template-independent tailing reaction. In some embodiments, the template-independent tailing reaction involves polynucleotide extension by a template-independent polymerase. In general, a template-independent polymerase is a polymerase that is capable of catalyzing a polynucleotide extension reaction in the absence of a template complementary to the sequence being polymerized. While template-independent polymerases do not require the presence of a template in order to catalyze the reaction, such that polymerization occurs independently of whether or not a template molecule is present, absence of a template is not necessarily required. Non-limiting examples of template-independent polymerases include terminal deoxynucleotidyl transferases (TdT; also known as DNA nucleotidylexotransferase (DNTT) or terminal transferase), poly-A polymerases, RNA-specific nucleotidyl transferases, poly(U) polymerases, and mutated or modified versions thereof. In some embodiments, the template-independent polymerase is a TDT. The template-independent polymerase can be from any suitable source. Specific non-limiting examples of template-independent polymerases include recombinantly produced calf thymus TDT and *E. coli* poly-A polymerase, both of which are commercially available.

In some embodiments, a tailing reaction comprises an adapter comprising an overhang that hybridizes to the tail. The overhang may hybridize to the tail during the polynucleotide extension reaction; however, in a template-independent polymerization reaction initiated by a template-independent polymerase, such hybridization does not negate the status of the reaction as template-independent. An adapter with an overhang comprises at least one single-stranded region (the overhang) and at least one double-stranded region (immediately adjacent to the overhang). An adapter can comprise an overhang on both ends, and involve the same or different strands. For example, a double-stranded region can be formed by hybridizing a short oligonucleotide in the middle of a longer oligonucleotide. As another example, two oligonucleotides can be hybridized to one another such that an overhang at one end is formed by one of the oligonucleotides, and an overhang at the other end is formed by the other oligonucleotide. In some embodiments, there is an overhang only at one end, such that the other end terminates in paired nucleotides (also referred to as a "blunt end"). An adapter can also be formed by hybridizing more than two oligonucleotides, and may comprise internal single-stranded regions between double-stranded regions (e.g., as in two short oligonucleotides hybridized to the same long oligonucleotide at regions that are one or more nucleotides apart along the long oligonucleotide). In some embodiments, there is only a single overhang on either the 5' or 3' end. In some embodiments, the overhang is a 3' overhang. In some embodiments, the adaptor has both a 3' overhang and a 5' overhang. Without being bound by a particular theory, the 5' overhang creates a recessive 3' end that can prevent a leaky tailing reaction on the adaptor itself. The 5' overhang creates a 3' recessive end on the other strand, which prevents a leaky tailing reaction on the adapter due to incomplete 3' end chemical blocking during oligonucleotide synthesis.

In general, an overhang that hybridizes to a particular tail comprises a sequence designed to be complementary to the tail to be polymerized. In some embodiments, the entire length of the overhang is designed to hybridize to the tail. The sequence designed to hybridize to the tail need not be perfectly complementary to the tail; rather, the overhang need only be designed to hybridize to the tail under a particular reaction condition, such as during the tailing reaction. In some embodiments, the overhang is designed to be perfectly complementary. In cases where a tail is polymerized from a pool of a single type of nucleotide (e.g., poly-A), designing a perfectly complementary overhang (or portion thereof) is relatively straightforward (e.g., poly-T in the case of poly-A).

In cases where a tail is polymerized from a pool of two or more types of polynucleotides, individual tail sequences can vary, such that an adapter overhang that is perfectly complementary to one individual tail will not be perfectly complementary to another. In some embodiments, a single adapter overhang sequence is designed to maximize complementarity with a tail polymerized from two or more nucleotides. For example, a tail polymerized from C and T with a C: T ratio of 5:1 could be designed to be poly-G. In such an example, a tail of 10 nucleotides would be expected to have an average of 2 mismatches along the same length of a poly-G adapter overhang. Alternatively, an adapter sequence can be expressed as containing one or more (or all) degenerate positions, selected based on degenerate positions of the tail to which it is designed to hybridize. For example, for a tail represented by the sequence "YYY," an overhang could be designed to have sequence "RRR." Where an overhang comprises one or more degenerate base positions, "the adapter" represent a pool of adapter oligonucleotides with each of the different nucleotides at each degenerate position represented in the pool. In a pool of adapter oligonucleotides, the relative representation of a particular nucleotide in the overhang, or the relative amount of one or more sequences in the pool can be modulated (e.g., to correspond to the relative amounts of nucleotides in the pool of nucleotides from which the tail is polymerized). For example, an oligonucleotide that forms the strand of the adapter forming the overhang can be polymerized from a pool of nucleotides complementary to the nucleotides of the tail, and in corresponding relative amounts (e.g., 9:1 G: A for a tail polymerized from a 9:1 C:T). As another example, an adapter designed to hybridize to a poly-C/T tail (e.g., 9:1 C:T) could be designed to be 10 nucleotides in length and comprising in equal amounts all possible overhangs having a single adenine, and optionally every sequence having two adenines. Other variations for designing an overhang that hybridizes to a tail polymerized from a given pool of nucleotides are possible.

In some embodiments, the length of the adapter's overhang is selected to control the length of the tail produced by the template-independent polymerase, particularly in cases where the polymerase lacks strand-displacement activity. In such embodiments, the double-stranded region of the adapter inhibits elongation of the tail when the tail is hybridized to the overhang. Inhibiting tail elongation does not necessarily require that all tails produced in the elongation reaction to be that same length as the overhang. Rather, tail elongation is considered to be inhibited by an adapter if the average tail length produced in the template-independent polymerization reaction is shorter than the average tail length produced in the absence of the adapter. In some embodiments, an adapter overhang is about or less than about 3, 4, 5, 6, 7, 8, 9, 10, 11, 12, 13, 14, 15, 20, 25, or more nucleotides in length. In some embodiments, the adapter overhang is between about 3-25, 5-20, or 10-15 nucleotides in length. In some embodiments, the overhang is about 6-12 nucleotides in length.

In methods comprising more than one adapter (e.g., a first adapter and a second adapter), the length and/or sequence of the adapters, or any portion thereof (e.g., an overhang, a double-stranded region, or some other sequence element, such as a primer binding site) can be the same or different. In some embodiments, the method comprises two tailing reactions that each comprise an adapter, and the two adapters have overhangs of equal lengths and/or the same sequence. In some embodiments, the method comprises two tailing reactions that each comprise an adapter, and the two adapters have overhangs of different lengths and/or different sequences. In some embodiments, the adapter is present in a tailing reaction in a relative molar amount of about or less than about 0.25-fold, 0.5-fold, 0.75-fold, 1-fold, 2-fold, 3-fold, 4-fold, 5-fold, 10-fold, or more with respect to the amount of target polynucleotides in the reaction. In some embodiments, the adapter is present in the tailing reaction at an approximately 1:1 molar ratio with respect to the target polynucleotides.

In some embodiments, an adapter comprises one or more of a variety of sequence elements, in addition to the overhang that hybridizes with the tail. Examples of additional sequence elements include, but are not limited to, one or more amplification primer annealing sequences or complements thereof, one or more sequencing primer annealing sequences or complements thereof, one or more index sequences (e.g., one or more sequences associated with a particular sample source or reaction that can be used to identify the origin of a target polynucleotide with which the index is associated), one or more common sequences shared among multiple different adapters or subsets of different adapters, one or more restriction enzyme recognition sites, one or more probe binding sites (e.g. for attachment to a sequencing platform, such as a flow cell for massive parallel sequencing, such as flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In some embodiments, an adapter is used to purify target polynucleotides to which they are attached, for example by using beads (particularly magnetic beads for ease of handling) that are coated with oligonucleotides comprising a complementary sequence to the adapter (or portion thereof) attached to a target polynucleotide. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. A sequence element may be of any suitable length, such as about or less than about 3, 4, 5, 6, 7, 8, 9, 10, 15, 20, 25, 30, 35, 40, 45, 50 or more nucleotides in length. Adapter oligonucleotides can have any suitable length, at least sufficient to accommodate the one or more sequence elements of which they are comprised. In some embodiments, adapters comprise oligonucleotides that are each independently selected to have a length of about or less than about 10, 15, 20, 25, 30, 35, 40, 45, 50, 55, 60, 65, 70, 75, or more nucleotides in length. In some embodiments, an adapter oligonucleotide is in the range of about 10 to 75 nucleotides in length, such as about 15 to 50 nucleotides in length. In some embodiments, an adapter comprises a double-stranded portion that is about or less than about 5, 10, 15, 20, 25, 30, 35, 40, 45, 50, 75, or more nucleotides in length.

In some embodiments, an adapter comprises one or more 3' ends that are not a substrate for polynucleotide extension, such as during a template-independent polymerization reaction. In such cases, the 3' end is referred to as being "blocked." In some embodiments, a 3' end that is blocked is the 3' end of the overhang that hybridizes to the tail formed during template-independent polymerization, such that the 3' end is not extended during the reaction. Various methods are available for forming a 3' end that cannot be extended, including, without limitation, incorporating at the 3' end a nucleotide that cannot be extended and modifying the 3' end nucleotide to render it unextendable. In some embodiments, the 3' end lacks a 3' hydroxyl group needed by a polymerase to covalently attach another nucleotide. In some embodiments, a blocking group is added to the terminal 3'-OH or 2'-OH in the adapter. Some non-limiting examples of blocking groups include an alkyl group, non-nucleotide linkers, a phosphate group, a phosphorothioate group, alkane-diol moieties, and an amino group. In some embodiments, the 3'-hydroxyl group is modified by substitution of hydrogen with fluorine or by formation of an ester, amide, sulfate or glycoside. In some embodiments, the 3'—OH group is replaced with hydrogen (to form a dideoxynucleotide). In some embodiments, the 3' end comprises a phosphate group.

In some embodiments, a strand of the adapter is ligated to a tail sequence, such as in a ligation reaction. In some embodiments, ligation occurs in the same reaction mixture as a tailing reaction. In some embodiments, reagents for carrying out a ligation reaction are included in a tailing reaction. In some embodiments, reagents for carrying out a ligation reaction are added to a reaction mixture after tailing is initiated or terminated. In some embodiments, ligation is effected by a ligase enzyme. A variety of ligase enzymes are available, non-limiting examples of which include NAD-dependent ligases including Taq DNA ligase, *Thermus filiformis* DNA ligase, *E. coli* DNA ligase, Tth DNA ligase, *Thermus scotoductus* DNA ligase (I and II), thermostable ligase, Ampligase thermostable DNA ligase, VanC-type ligase, and 9° N DNA Ligase; and ATP-dependent ligases including T4 RNA ligase, T4 DNA ligase, T3 DNA ligase, T7 DNA ligase, Pfu DNA ligase, DNA ligase 1, DNA ligase III, and DNA ligase IV.

In some embodiments, target polynucleotides are treated to differentially modify methylated cytosines or unmethylated cytosines. In some embodiments, treatment to distinguish cytosine methylation status is performed prior to an amplification reaction, such as after a first ligation reaction involving the target polynucleotides but before subsequent amplification, during the ligation reaction, or before the ligation reaction (e.g. before tailing target polynucleotides, or as part of sample preparation). In some embodiments, treatment to distinguish cytosine methylation status is performed on a portion of target polynucleotides from a particular source, and another portion from the same source is untreated (e.g., as in different aliquots from a common solution), such that the treated and untreated samples can be subsequently compared. In certain processes, comparison facilitates identifying cytosine methylation status, such as in identifying sequence differences produced as a result of treatment. A variety of treatment processes for differentially modifying methylated or unmethylated cytosines are available. An example of a reagent that selectively modifies methylated cytosines is the TET family of proteins (e.g., TET1, TET2, TET3, and CSSC4), which convert the cytosine nucleotide 5-methylcytosine into 5-hydroxymethylcytosine by hydroxylation. 5-hydroxymethylcytosine can be selectively modified, such as by treatment with metal (VI) oxo complexes (e.g., manganate ($Mn(VI)O_4^{2-}$), ferrate ($Fe(VI)O_4^{2-}$), osmate ($Os(VI)O_4^{2-}$), ruthenate ($Ru(VI)O_4^{2-}$), or molybate ($Mo(VI)O_4^{2-}$)). Treatment with metal (VI)oxo complexes oxidizes 5-hydroxymethylcytosine (5hmC) residues into 5-formylcytosine (5fC) residues, which can be subsequently converted into uracil by bisulfite treatment. In some embodiments, treatment to differentially modify methylated cytosines or unmethylated cytosines comprises treating the target polynucleotides with sodium hydrogen sulfite (bisulfite), which sulfonates unmethylated cytosine but does not efficiently sulfonate methylated cytosine. The sulfonated unmethylated cytosine is prone to spontaneous deamination, which yields sulfonated uracil. The sulfonated uracil can then be disulfonated to uracil at high pH. The base-pairing properties of the pyrimidines uracil and cytosine are fundamentally different: uracil in DNA is recognized as the equivalent of thymine and therefore is paired with adenine during hybridization or polymerization of DNA, whereas cytosine is paired with guanosine during hybridization or polymerization of DNA. Performance of genomic sequencing or PCR on bisulfite treated DNA can therefore be used to distinguish unmethylated cytosine in the genome, which has been converted to uracil, versus methylated cytosine, which has remained unconverted. Such techniques are amenable to large-scale screening approaches when combined with other technologies such as microarray hybridization and high-throughput sequencing. Examples of processes for differentially modifying and distinguishing methylated or unmethylated cytosines are described in, e.g., U.S. Pat. Nos. 9,822,394, 9,115,386, and US20150299781, which are incorporated herein by reference.

In some embodiments, target polynucleotides comprising a first tail ligated to a strand of a first adapter, resulting from being subjected to a first tailing reaction and a first ligation reaction, are amplified. In some embodiments, amplification comprises extending a first primer hybridized to the strand of the first adapter ligated in an earlier ligation reaction. In such cases, the primer comprises a sequence that is hybridizable to at least a portion of the ligated strand of the adapter. In some embodiments, the hybridizable sequence is complementary to the sequence to which it hybridizes. In some embodiments, the primer hybridizes to a common sequence present in all first adapter polynucleotides ligated during the ligation reaction. In some embodiments, the hybridizable portion of the primer is about or more than about 10, 15, 20, 25, 30, 35, 45, 50, or more nucleotides in length. Typically, the hybridizable portion of a primer comprises the 3' end of the primer. In some embodiments, the first primer comprises one or more additional sequence elements. Examples of additional sequence elements include, but are not limited to, one or more primer annealing sequences or complements thereof (e.g., a sequencing primer), one or more index sequences (e.g., one or more sequences associated with a particular sample source or reaction that can be used to identify the origin of a target polynucleotide with which the index is associated), one or more restriction enzyme recognition sites, one or more probe binding sites (e.g. for attachment to a sequencing platform, such as a flow cell for massive parallel sequencing, such as flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. A sequence element may be of any suitable length, such as about or less than about 3, 4, 5, 6, 7, 8, 9, 10, 15, 20, 25, 30, 35, 40, 45, 50 or more nucleotides in length.

A variety of amplification processes are available for amplifying target polynucleotides comprising a first tail ligated to a strand of a first adapter, and include both exponential and non-exponential (e.g., linear) processes. In an exponential amplification, a primer extension product is used as the template for producing a further primer extension product that is complementary to the first. Linear amplification reactions, by contrast, are typically designed to minimize or eliminate formation of primer extension products templated off of other primer extension products formed during the reaction. In some embodiments, amplification of target polynucleotides comprising a first tail ligated to a strand of a first adapter is a linear amplification. The first step of amplification comprises primer annealing, in which the first primer hybridizes to the strand of the adapter ligated to the tail. In cases where the primer hybridization site comprises a double-stranded portion of the adapter, the hybridization site in the template strand will first be exposed. Exposure of the hybridization site can be achieved by denaturing and/or degrading the non-template strand of the adapter. Denaturation can comprise heat denaturation, such has heating to about or more than about 90° C. or 95° C. for a period of time (e.g., about or more than about 1, 2, 3, 4, 5, 10, or more minutes). Various processes are available for degrading a non-template strand of the adapter, and can be appropriately selected based on the composition of the strand to be degraded. For example, where the strand comprises one or more RNA bases, a ribonuclease (e.g., RNase H or RNase A) can be used to degrade the non-template strand. As a further example, where the non-template strand of the adapter comprises one or more uracil bases, degradation can be effected by addition of Uracil-Specific Excision Reagent (USER) enzyme, which is a mixture of Uracil DNA glycosylase (UDG) and the DNA glycosylase-lyase Endonuclease VIII.

A variety of processes for linear amplification are available, and examples include isothermal and non-isothermal processes. In a non-isothermal process, the process includes denaturation and primer extension steps carried out at different temperatures. Denaturation releases a primer extension product formed on a template, freeing the primer hybridization site for hybridization with another copy of the primer. Extension of the further copy of the first primer produces another primer extension product from the same template, and the whole process can be repeated through several "cycles" of denaturation and extension. In some embodiments, a non-isothermal process is used, and the number of cycles is about or at least about 2, 5, 10, 15, 20, 25, or more. An example of an isothermal linear amplification process is single primer isothermal amplification (SPIA). In general, SPIA comprises extension of a composite primer having a 3' DNA portion and a 5' RNA portion, degradation of the RNA portion by RNase H, annealing of another copy of the composite primer, and extension of the further copy of the composite primer by a polymerase with strand-displacement activity, all of which can take place at the same temperature. Further descriptions of these and other amplification reactions can be found, e.g., in US20170362636 A1, which is hereby incorporated by reference. In some embodiments, amplification produces a plurality of single-stranded copies complementary to the template target polynucleotides, comprising sequences complementary to the first tail and at least a portion of the ligated strand of the first adapter. In some embodiments, amplification conditions are selected to produce about or less than about 1, 2, 3, 4, 5, 6, 7, 8, 9, 10, 15, 20, 25, 30, 40, 50, 100, 200, 500, or more copies of a target polynucleotide.

In some embodiments, amplification products of the amplification reaction with the first primer are subjected to a tailing reaction, referred to as the second tailing reaction. The second tailing reaction adds a second tail to each of a plurality of the amplified target polynucleotides by template-independent polymerization. As with the first tailing reaction, the length and nucleotide sequence of the tail will depend, in part, on the type of nucleotides from which the tail is polymerized (e.g., 1, 2, 3, or 4 of A, T, G, and C), the duration of the reaction, the polymerase used, and the presence of other reagents (e.g. an adapter comprising an overhang that hybridizes to the second tail during the polymerization reaction). Considerations concerning formation and composition of tails generally, as provided above, are equally applicable with respect to the second tailing reaction. In some embodiments, the tail is polymerized only to the 3' end of one or more amplified target polynucleotides. In some embodiments, the second tailing reaction is designed to produce a tail having the same or substantially the same sequence as the first tail, or a sequence complementary thereto. For example, the first a second tail can be formed from a pool of only adenine bases, forming poly-A tails. Where the second tailing reaction is performed on amplification products complementary to the tailed target polynucleotide templates, the resulting second-tailed polynucleotide would comprise a poly-A tail at one end and a poly-T tail adjacent to at least a portion of the complement of the adapter strand to which the first tail was hybridized. As a further example, the first tail could be a poly-A tail and the second tail could be a poly-T tail. Where the second tailing reaction is performed on amplification products complementary to the tailed target polynucleotide templates, the result in this example would be a polynucleotide having two poly-T stretches, one from the first tail and one from the second. In some embodiments, the second tailing reaction is designed to produce a tail having a different sequence from the first tail, such as by using one or more nucleotides in the nucleotide pool for the second tailing reaction that were not used in the pool used in the first tailing reaction. Various combinations of different first a second tails are possible. Non-limiting examples of tail combinations include: (a) one tail consists of one type of nucleotide, and another tail consists of another type of nucleotide; (b) one tail consists of one type of nucleotide, and another tail comprises or consists of two or more types of nucleotides; (c) both tails comprise or consist of two or more types of nucleotides, but each comprises at least one type of nucleotide not contained in the other. In some embodiments, the first tail, the second tail, or both are selected from the group consisting of poly-A, poly-C, and poly-C/T.

In some embodiments, the second tailing reaction comprises an adapter (referred to as the second adapter) comprising an overhang that hybridizes to the second tail. The overhang may hybridize to the tail during the polynucleotide extension reaction; however, in a template-independent polymerization reaction initiated by a template-independent polymerase, such hybridization does not negate the status of the reaction as template-independent. The second adapter comprises at least one single-stranded region (the overhang) and at least one double-stranded region (immediately adjacent to the overhang). The second adapter can comprise an overhang on both ends, and involve the same or different strands. For example, a double-stranded region can be formed by hybridizing a short oligonucleotide in the middle of a longer oligonucleotide. As another example, two oligonucleotides can be hybridized to one another such that an overhang at one end is formed by one of the oligonucleotides, and an overhang at the other end is formed by the other oligonucleotide. In some embodiments, there is an overhang only at one end, such that the other end terminates in paired nucleotides (also referred to as a "blunt end"). An adapter can also be formed by hybridizing more than two oligonucleotides, and may comprise internal single-stranded regions between double-stranded regions (e.g., as in two short oligonucleotides hybridized to the same long oligonucleotide at regions that are one or more nucleotides apart along the long oligonucleotide). In some embodiments, there is only a single overhang on either the 5' or 3' end. In some embodiments, the overhang is a 3' overhang. In some embodiments, the adaptor has both a 3' overhang and a 5' overhang. If a first and second adaptor is used, both adaptors can have a both a 5' overhang and a 3' overhang.

Considerations concerning formation and composition of adapters generally, including its relationship to a tail, as provided above, are equally applicable with respect to the second adapter and its relationship to the second tail in the second tailing reaction. These considerations include, but are not limited to, overhang length, overhang sequence, nucleotide composition, optional use of a blocked 3' end, and the optional inclusion of one or more sequence elements in addition to the overhang. In some embodiments, the second adapter is the same as the first adapter. In some embodiments, at least a portion of the second adapter differs from the first adapter. In some embodiments, the first and second adapter comprise one or more portions in common, while differing in other portions. For example, the first and second adapter may comprise a common primer binding sequence, designed such that after attachment of the second adapter to the amplified target polynucleotides, further exponential amplification can be achieved with a single primer that hybridizes to that common primer binding sequence or complement thereof. In some embodiments, both the first and second adapters comprise a primer binding sequence that is designed for exponential amplification by different primers.

In some embodiments, a strand of the second adapter is ligated to the second tail sequence, such as in a ligation reaction (referred to as the second ligation reaction). In some embodiments, ligation occurs in the same reaction mixture as the second tailing reaction. In some embodiments, reagents for carrying out the second ligation reaction are included in the second tailing reaction. In some embodiments, reagents for carrying out the second ligation reaction are added to a reaction mixture after the second tailing is initiated or terminated. In some embodiments, ligation is effected by a ligase enzyme, examples of which are provided above. In some embodiments, products of the second ligation reaction are a collection of polynucleotides, each comprising the following elements, from 5' to 3': (a) a sequence complementary to at least a portion of the ligated strand of the first adapter, (b) a sequence complementary to the first tail, (c) a sequence complementary to a target polynucleotide, (d) the second tail, and (e) the ligated strand of the second adapter. For simplicity, such ligation products, as well as amplification products thereof, will be referred to as "dual-adapted" or "double-adapted" target polynucleotides, even though it is understood that element (a) might not comprise the entire ligated adapter strand of the first adapter, element (b) is a complementary copy of a target polynucleotide, and element (e) might not comprise the entire ligated adapter strand (e.g., in the case of an amplification product of the second ligation product). Where a plurality of different target polynucleotides are represented in the collection of double-adapted target polynucleotides, the collection may be referred to as a library.

In some embodiments, the double-adapted target polynucleotides are amplified in an amplification reaction. In some embodiments, the amplification comprises extending a second primer hybridized to the ligated strand of the second adapter. In such cases, the second primer comprises a sequence that is hybridizable to at least a portion of the ligated strand of the second adapter. In some embodiments, the hybridizable sequence is complementary to the sequence to which it hybridizes. In some embodiments, the primer hybridizes to a common sequence present in all second adapter polynucleotides ligated during the second ligation reaction. In some embodiments, the hybridizable portion of the primer is about or more than about 10, 15, 20, 25, 30, 35, 45, 50, or more nucleotides in length. Typically, the hybridizable portion of a primer comprises the 3' end of the primer. In some embodiments, the second primer comprises one or more additional sequence elements. Examples of additional sequence elements include, but are not limited to, one or more primer annealing sequences or complements thereof (e.g., a sequencing primer), one or more index sequences (e.g., one or more sequences associated with a particular sample source or reaction that can be used to identify the origin of a target polynucleotide with which the index is associated), one or more restriction enzyme recognition sites, one or more probe binding sites (e.g. for attachment to a sequencing platform, such as a flow cell for massive parallel sequencing, such as flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. A sequence element may be of any suitable length, such as about or less than about 3, 4, 5, 6, 7, 8, 9, 10, 15, 20, 25, 30, 35, 40, 45, 50 or more nucleotides in length.

Amplification with the second primer can be exponential or non-exponential (e.g., linear). Amplification can be isothermal or non-isothermal. In some embodiments, products of the second ligation reaction are substantially linear, and amplification consists of rendering the ligation products double-stranded by extension of the second primer. In some embodiments, the second primer is the same as the first primer, or comprises the same hybridizable sequence as the first primer. In some embodiments, the second primer differs from the first primer, such as with regard to the hybridizable sequence. In some embodiments, the amplification reaction comprises the second primer and a reverse primer that differs from the second primer. In some embodiments, the reverse primer is the first primer (described above with regard to amplifying products of the first ligation). In some embodiments, the reverse primer hybridizes to a sequence that is downstream with respect to where the first primer hybridizes (also referred to as "nested"), and may optionally include one or more additional sequence elements (e.g., any one or more primer sequence element described above). In some embodiments, the reverse primer comprises all or a portion of the hybridizable sequence of the first primer, and one or more sequence elements that differ from the first primer (e.g., any one or more primer sequence element described above). The first step of amplification comprises primer annealing, in which the second primer hybridizes to the strand of the second adapter ligated to the second tail. In cases where the primer hybridization site comprises a double-stranded portion of the second adapter, the hybridization site in the template strand will first be exposed. Exposure of the hybridization site can be achieved by denaturing and/or degrading the non-template strand of the adapter, example processes for which are described above. Non-limiting examples of linear amplification processes are described above. Non-limiting examples of exponential amplification processes are described above, and in more detail below.

In some embodiments, double-adapted target polynucleotides are amplified in an amplification reaction with a third primer and a fourth primer, wherein (i) the third primer hybridizes to a complement of at least a portion of the first primer, and (ii) the fourth primer hybridizes to a complement of at least a portion of the second primer. In some embodiments, this amplification step replaces the step of amplification with the second primer, in which case the third and fourth primers are analogous to the second primer and reverse primer described above. In some embodiments, amplification with the third and fourth primers is in addition to the amplification with the second primer (which may or may not have included amplification with the reverse primer). In some embodiments, the hybridizable sequence of the third primer is different from the hybridizable sequence of the first primer, and/or the hybridizable sequence of the fourth primer is different from the hybridizable sequence of the second primer. In some embodiments, the third primer is nested with regard to the first primer and/or the fourth primer is nested with regard to the second primer.

In some embodiments, the hybridizable portion of the third and/or fourth primer is independently selected from a length of about or more than about 10, 15, 20, 25, 30, 35, 45, 50, or more nucleotides. Typically, the hybridizing portion of a primer comprises the 3' end of the primer. In some embodiments, the third and/or fourth primer comprises one or more additional sequence elements (e.g., any one or more primer sequence element described above). A sequence element may be of any suitable length, such as about or less than about 3, 4, 5, 6, 7, 8, 9, 10, 15, 20, 25, 30, 35, 40, 45, 50 or more nucleotides in length. In some embodiments, the third primer and fourth primer are different, such as with regard to one or more of total length, sequence, sequence of the hybridizable sequence, presence of one or more sequence elements, length of one or more sequence elements, and sequence of one or more sequence elements.

In some embodiments, the third primer, the fourth primer, or both comprise an index sequence (also referred to as a barcode, or simply "index"). In general, the term "index" refers to a known nucleic acid sequence that allows some feature of a polynucleotide with which the index is associated to be identified. In some embodiments, the feature of the polynucleotide to be identified is the source (e.g. sample, sample fraction, or reaction) from which the polynucleotide is derived. In some embodiments, indexes are about or at least about 3, 4, 5, 6, 7, 8, 9, 10, 11, 12, 13, 14, 15, or more nucleotides in length. In some embodiments, indexes are shorter than 10, 9, 8, 7, 6, 5, or 4 nucleotides in length. In some embodiments, indexes associated with some polynucleotides are of different lengths than indexes associated with other polynucleotides. In general, indexes are of sufficient length and comprise sequences that are sufficiently different to allow the identification of sources based on indexes with which they are associated, particularly from among different indexes associated with polynucleotides from different sources in a mixture. In some embodiments, an index, and the source with which it is associated, can be identified accurately after the mutation, insertion, or deletion of one or more nucleotides in the index sequence, such as the mutation, insertion, or deletion of 1, 2, 3, 4, 5, 6, 7, 8, 9, 10, or more nucleotides. In some embodiments, each index in a plurality of indexes differ from every other index in the plurality at least three nucleotide positions, such as at least 3, 4, 5, 6, 7, 8, 9, 10, or more nucleotide positions. A plurality of indexes may be represented in a pool of polynucleotides from different sources, each source comprising polynucleotides comprising one or more indexes that differ from the indexes contained in the polynucleotides derived from the other sources in the pool. It is emphasized here that indexes need only be unique within a given experiment. Thus, the same index may be used to tag a different sample being processed in a different experiment. In addition, in certain experiments, a user may use the same index to tag a subset of different samples within the same experiment. For example, all samples derived from individuals having a specific phenotype may be tagged with the same index, e.g., all samples derived from control (or wild-type) subjects can be tagged with a first index while subjects having a disease condition can be tagged with a second index (different than the first index). As another example, it may be desirable to tag different samples derived from the same source with different indexes (e.g., samples derived over time, derived from different sites within a tissue, or different aliquots of the same sample subjected to different treatments (e.g., with or without bisulfite treatment)). Once indexes are attached, pools of polynucleotides comprising different indexes can be combined for further processing, such as amplification and/or sequencing. Upon sequencing, the indexes can be used to group sequences derived from the same source, thereby associating sequences having one or more particular indexes with that source. In some embodiments, a method comprises identifying the sample from which a target polynucleotide is derived based on an index sequence to which the target polynucleotide (or complement or derivative thereof) is joined. Examples of indexes and their use in identifying sample sources can be found in US20140121116, US20150087535, and US20120071331, which are hereby incorporated by reference.

In some embodiments, the method comprises an exponential amplification step. Exponential amplification includes, for example, reactions comprising a forward and reverse primer, such that the primer extension products of the forward primer serve as templates for primer extension of the reverse primer, and vice versa. Amplification may be isothermal or non-isothermal. A variety of methods for amplification of target polynucleotides are available, and include without limitation, methods based on polymerase chain reaction (PCR). Conditions favorable to the amplification of target sequences by PCR can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be suitably altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, or more steps. Steps can comprise any temperature or gradient of temperatures, suitable for achieving the purpose of the given step, including but not limited to, 3' end extension, primer annealing, primer extension, and strand denaturation. Steps can be of any duration, including but not limited to about or less than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. In some embodiments, amplification is performed before or after pooling of target polynucleotides (e.g., double-adapter target polynucleotides) from independent samples or aliquots. Non-limiting examples of PCR amplification techniques include quantitative PCR (qPCR or real-time PCR), digital PCR, and target-specific PCR.

Non-limiting examples of polymerase enzymes for use in PCR include thermostable DNA polymerases, such as *Thermus thermophilus* HB8 polymerase; *Thermus oshimai* polymerase; *Thermus scotoductus* polymerase; *Thermus thermophilus* polymerase; *Thermus aquaticus* polymerase (e.g., AmpliTaq® FS or Taq (G46D; F667Y); *Pyrococcus furiosus* polymerase; *Thermococcus* sp. (strain 9° N-7) polymerase; Tsp polymerase; Phusion High-Fidelity DNA Polymerase (ThermoFisher); and mutants, variants, or derivatives thereof. Further examples of polymerase enzymes useful for some PCR reactions include, but are not limited to, DNA polymerase I, mutant DNA polymerase I, Klenow fragment, Klenow fragment (3' to 5' exonuclease minus), T4 DNA polymerase, mutant T4 DNA polymerase, T7 DNA polymerase, mutant T7 DNA polymerase, phi29 DNA polymerase, and mutant phi29 DNA polymerase. In some embodiments, a hot start polymerase is used. A hot start polymerase is a modified form of a DNA Polymerase that requires thermal activation. Typically, the hot start enzyme is provided in an inactive state. Upon thermal activation the modification or modifier is released, generating active enzyme. A number of hot start polymerases are available from various commercial sources, such as Applied Biosystems; Bio-Rad; ThermoFisher; New England Biolabs; Promega; QIAGEN; Roche Applied Science; Sigma-Aldrich; and the like.

In some embodiments, primer extension and amplification reactions comprise isothermal reactions. Non-limiting examples of isothermal amplification technologies are ligase chain reaction (LCR) (see e.g., U.S. Pat. Nos. 5,494,810 and 5,830,711); transcription mediated amplification (TMA) (see e.g., U.S. Pat. Nos. 5,399,491, 5,888,779, 5,705,365, 5,710,029); nucleic acid sequence-based amplification (NASBA) (see e.g., U.S. Pat. No. 5,130,238); signal mediated amplification of RNA technology (SMART) (see e.g., Wharam et al., Nucleic Acids Res. 2001, 29, e54); strand displacement amplification (SDA) (see e.g., U.S. Pat. No. 5,455,166); thermophilic SDA (see e.g., U.S. Pat. No. 5,648,211); rolling circle amplification (RCA) (see e.g., U.S. Pat. No. 5,854,033); loop-mediated isothermal amplification of DNA (LAMP) (see e.g., U.S. Pat. No. 6,410,278); helicase-dependent amplification (HDA) (see e.g., U.S. patent application No. 20040058378); exponential amplification methods based on SPIA (see e.g., U.S. Pat. No. 7,094,536); and circular helicase-dependent amplification (cHDA) (e.g., U.S. patent application Ser. No. 20/100,075384).

In some embodiments, methods comprise sequencing double-adapted polynucleotides. In some embodiments, the methods comprise sequencing products of the amplification with the second primer. In some embodiments, the methods comprise sequencing products of amplification with the third and fourth primer. A variety of sequencing methodologies are available, particularly high-throughput sequencing methodologies. Examples include, without limitation, sequencing systems manufactured by Illumina (sequencing systems such as HiSeq® and MiSeq®), Life Technologies (Ion Torrent®, SOLID®, etc.), Roche's 454 Life Sciences systems, Pacific Biosciences systems, nanopore sequencing platforms by Oxford Nanopore Technologies, etc. In some embodiments, sequencing comprises producing reads of about or more than about 50, 75, 100, 125, 150, 175, 200, 250, 300, or more nucleotides in length. In some embodiments, sequencing comprises a sequencing by synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate, an example description of which can be found in U.S. Pat. No. 6,210,891. According to some sequencing methodologies, the primer/template/polymerase complex is immobilized upon a substrate and the complex is contacted with labeled nucleotides. Further non-limiting examples of sequencing technologies are described in US20160304954, U.S. Pat. Nos. 7,033,764, 7,416,844, and WO2016077602.

In some cases, sequencing reactions of various types, as described herein, may comprise a variety of sample processing units. Sample processing units may include but are not limited to multiple lanes, multiple channels, multiple wells, and other mean of processing multiple sample sets substantially simultaneously. Additionally, the sample processing unit may include multiple sample chambers to facilitate processing of multiple runs simultaneously. In some embodiments, simultaneous sequencing reactions are performed using multiplex sequencing. In some embodiments, polynucleotides are sequenced to produce about or more than about 5000, 10000, 50000, 100000, 1000000, 5000000, 10000000, or more sequencing reads in parallel, such as in a single reaction or reaction vessel. Subsequent data analysis can be performed on all or part of the sequencing reactions. Where polynucleotides are associated with an index sequence, data analysis can comprise grouping sequences based on index sequence for analysis together, and/or comparison to sequences associated with one or more different indexes.

In some embodiments, sequence analysis comprises comparison of one or more reads to a reference sequence (e.g., a control sequence, sequencing data for a reference population, sequencing data for a different tissue of the same subject, sequencing data for the same subject at another time point, or a reference genome), such as by performing an alignment. In a typical alignment, a base in a sequencing read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability. An indel deducts from an alignment score by a gap penalty. Gap penalties and substitution probabilities can be based on empirical knowledge or a priori assumptions about how sequences mutate. Their values affect the resulting alignment. Examples of algorithms for performing alignments include, without limitation, the Smith-Waterman (SW) algorithm, the Needleman-Wunsch (NW) algorithm, algorithms based on the Burrows-Wheeler Transform (BWT), and hash function aligners such as Novoalign (Novocraft Technologies; available at www.novocraft.com), ELAND (Illumina, San Diego, Calif.), SOAP (available at soap.genomics.org.cn), and Maq (available at maq.sourceforge.net). One exemplary alignment program, which implements a BWT approach, is Burrows-Wheeler Aligner (BWA) available from the SourceForge web site maintained by Geeknet (Fairfax, Va.). An alignment program that implements a version of the Smith-Waterman algorithm is MUMmer, available from the SourceForge web site maintained by Geeknet (Fairfax, Va.). Other non-limiting examples of alignment programs include: BLAT from Kent Informatics (Santa Cruz, Calif.); SOAP2, from Beijing Genomics Institute (Beijing, Conn.) or BGI Americas Corporation (Cambridge, Mass.); Bowtie; Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK), Clustal Omega, from University College Dublin (Dublin, Ireland); and ClustalW or ClustalX from University College Dublin (Dublin, Ireland).

In some embodiments, amplification products are sequenced to detect a sequence variant, e.g., insertions, deletions, substitutions, duplications, translocations, and/or rare somatic mutations, with respect to a reference sequence or in a background of no mutations. In some embodiments, the sequence variant is correlated with a disease or trait. In some embodiments, the sequence variant is not correlated with a disease or trait. In general, sequence variants for which there is statistical, biological, and/or functional evidence of association with a disease or trait are referred to as "causal genetic variants." A single causal genetic variant can be associated with more than one disease or trait. In some cases, a causal genetic variant is associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphisms, and heritable epigenetic modifications (for example, DNA methylation). A causal genetic variant can comprise a set of closely related genetic variants. Some causal genetic variants may exert influence as sequence variations in RNA. At this level, some causal genetic variants are also indicated by the presence or absence of a species of RNA. Some causal genetic variants result in sequence variations in protein. A number of causal genetic variants have been reported. An example of a causal genetic variant that is a SNP is the HbS variant of hemoglobin that causes sickle cell anemia. An example of a causal genetic variant that is a DIP is the delta-F508 mutation of the CFTR gene which causes cystic fibrosis. An example of a causal genetic variant that is a CNV is trisomy 21, which causes Down's syndrome. An example of a causal genetic variant that is an STR is the tandem repeat that causes Huntington's disease. Additional non-limiting examples of causal genetic variants are described in US2014121116.

Examples of diseases and gene targets with which a causal genetic variant may be associated include, but are not limited to, 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, one or more other types of cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn's Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type 1b, Glycogen Storage Disease Type II, Glycogen Storage Disease Type III, Glycogen Storage Disease Type V, *Gracile* Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia *Punctata* Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis, and Zellweger Syndrome Spectrum.

Examples of sequence variants associated with cancers include, but are not limited to, sequence variants in the PIK3CA gene (found in, e.g., colorectal cancers; most commonly located within two "hotspot" areas within exon 9 (the helical domain) and exon 20 (the kinase domain); position 3140 may be specifically targeted); sequence variants in the BRAF gene (found in, e.g., malignant melanomas, including melanomas derived from skin without chronic sun-induced damage, especially missense mutation resulting in V600E); sequence variants in the EGFR gene (found in, e.g., Non-Small Cell Lung Cancer, particularly within EGFR exons 18-21, and including exon 19 deletions and exon 21 L858R point mutations); sequence variants in the KIT gene (found in, e.g., Gastrointestinal Stromal Tumor (GIST), especially in juxtamembrane domain (exon 11), extracellular dimerization motif (exon 9), tyrosine kinase 1 (TK1) domain (exon 13), and tyrosine kinase 2 (TK2) domain and activation loop (exon 17). In some embodiments, sequence variants in one or more genes associated with cancer are identified. Non-limiting examples of genes associated with cancer include PTEN; ATM; ATR; EGFR; ERBB2; ERBB3; ERBB4; Notch1; Notch2; Notch3; Notch4; AKT; AKT2; AKT3; HIF; HIFla; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF; IGF Receptor; Igf1 (4 variants); Igf2 (3 variants); Igf 1 Receptor; Igf 2 Receptor; Bax; Bc12; caspases family (9 members: 1, 2, 3, 4, 6, 7, 8, 9, 12); Kras; and Apc.

In some embodiments, methods of the invention have a high sensitivity for detecting nucleic acid species that are present in relatively low abundance. In some embodiments, the low abundance species is a contaminant (e.g., in food or water), a particular bacterium in a complex population (e.g., in environmental testing), and nucleic acids associated with disease (e.g. infection, or a causal genetic variant). In some embodiments, the methods detect nucleic acid species (e.g., a mutant form of a reference polynucleotide) present at about or less than about 1 in 1000, 1 in 5000, 1 in 10000, 1 in 20000, or lower.

In some embodiments, methods further comprise detecting presence or absence of disease, such as cancer or infection, in a subject. Cancer cells, as most cells, can be characterized by a rate of turnover, in which old cells die and are replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various causal genetic variants, such as copy number variation as well as rare mutations. This phenomenon may be used to detect the presence or absence of cancer in a subject using the methods and systems described herein. In some cases, cancer is detected before symptoms or other hallmarks of disease occur. The types and number of cancers that may be detected include, but are not limited to, blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like. In some embodiments, the systems and methods described herein are used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer. Progression of cancer development and/or response to treatment regimen can be followed by detecting appearance, disappearance, or changes in relative amounts of certain causal genetic variants over time.

In one aspect, the present disclosure provides compositions for use in or produced by methods described herein, including with respect to any of the various other aspects and embodiments of this disclosure. Compositions of the disclosure can comprise any one or more of the elements described herein. In some embodiments, compositions include one or more of the following: one or more pools of nucleotides from which a tail can be polymerized, one or more adapters comprising a 3' overhang that hybridizes to a tail, one or more reagents for differentially modifying methylated or unmethylated cytosines, one or more amplification primers, one or more sequencing primers, one or more enzymes (e.g. one or more of a polymerase, a reverse transcriptase, a ligase, a ribonuclease, and a glycosylase), one or more buffers (e.g. sodium carbonate buffer, a sodium bicarbonate buffer, a borate buffer, a Tris buffer, a MOPS buffer, a HEPES buffer), reagents for utilizing any of these, reaction mixtures comprising any of these, and instructions for using any of these. In some embodiments, a polynucleotide produced according to a method described herein is provided.

In one aspect, the present disclosure provides reaction mixtures for use in or produced by methods described herein, including with respect to any of the various other aspects of this disclosure. In some embodiments, the reaction mixture comprises one or more compositions described herein.

In one aspect, the present disclosure provides kits for use in any of the methods described herein, including with respect to any of the various other aspects of this disclosure. In some embodiments, the kit comprises one or more compositions described herein. Elements of the kit can further be provided, without limitation, in any amount and/or combination (such as in the same kit or same container). In some embodiments, kits comprise additional agents for use according to the methods of the invention. Kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained. In some embodiments, a kit comprises: (a) a template-independent polymerase; (b) a first pool of nucleotides that can be polymerized by the template-independent polymerase; (c) a second pool of nucleotides that can be polymerized by the template-independent polymerase; (d) a first adapter comprising an overhang that is hybridizable to tails formed by polymerizing the first pool of polynucleotides; and (e) a second adapter comprising an overhang that is hybridizable to tails formed by polymerizing the second pool of polynucleotides, wherein the second adapter comprises a different sequence than the first adapter. In some embodiments, the kit further comprises one or more primers. Examples of polymerases, nucleotide pools, adapters, and primers are disclosed herein, including with regard to the various methods of the present disclosure.

In one aspect, the present disclosure provides systems, such as computer systems, for implementing methods described herein, including with respect to any of the various other aspects of this disclosure. It should be understood that it is not practical, or even possible in most cases, for an unaided human being to perform computational operations involved in some embodiments of methods disclosed herein. For example, mapping a single 30 bp read from a sample to any one of the human chromosomes might require years of effort without the assistance of a computational apparatus. Of course, the challenge of unaided sequence analysis and alignment is compounded in cases where reliable calls of low allele frequency mutations require mapping thousands (e.g., at least about 10,000) or even millions of reads to one or more chromosomes. Accordingly, some embodiments of methods described herein are not capable of being performed in the human mind alone, or with mere pencil and paper, but rather necessitate the use of a computational system, such as a system comprising one or more processors programmed to implement one or more analytical processes.

In some embodiments, the disclosure provides tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In some embodiments, the data or information employed in methods and systems disclosed herein are provided in an electronic format. Examples of such data or information include, but are not limited to, sequencing reads derived from a nucleic acid sample, reference sequences (including reference sequences providing solely or primarily polymorphisms), sequences of one or more oligonucleotides used in the preparation of the sequencing reads (including portions thereof, and/or complements thereof), calls such as cancer diagnosis calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In some embodiments, provided herein is a computer program product for generating an output indicating the sequences of polynucleotides in a test sample. The computer product may contain instructions for performing any one or more of the above-described methods for preparing a library of polynucleotides, and optionally determining polynucleotide sequences. As explained, the computer product may include a non-transitory and/or tangible computer readable medium having a computer executable or compilable logic (e.g., instructions) recorded thereon for enabling a processor to determine a sequence of interest. In one example, the computer product includes a computer readable medium having a computer executable or compilable logic (e.g., instructions) recorded thereon for enabling a processor to diagnose a condition and/or determine a nucleic acid sequence of interest.

In some embodiments, methods described herein (or portions thereof) are performed using a computer processing system which is adapted or configured to perform a method as described herein. In one embodiment, the system includes a sequencing device adapted or configured for sequencing polynucleotides to obtain the type of sequence information described elsewhere herein, such as with regard to any of the various aspects described herein. In some embodiments, the apparatus includes components for processing the sample, such as liquid handlers and sequencing systems, comprising modules for implementing one or more steps of any of the various methods described herein (e.g. sample processing, polynucleotide purification, and various reactions (e.g. tailing reactions, ligations reactions, amplification reactions, and sequencing reactions).

In some embodiments, sequence or other data is input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store read counts for various chromosomes or genomes, etc. The memory may also store various routines and/or programs for analyzing the sequence or mapped data. In some embodiments, the programs/routines include programs for performing statistical analyses.

In one example, a user provides a polynucleotide sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet, which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods comprise collecting data regarding a plurality of polynucleotide sequences (e.g., reads, and/or reference chromosome sequences) and sending the data to a computer or other computational system. For example, the computer can be connected to laboratory equipment, e.g., a sample collection apparatus, a nucleotide amplification apparatus, or a nucleotide sequencing apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data.

Among the types of electronically formatted data that may be stored, transmitted, analyzed, and/or manipulated in systems, apparatus, and methods disclosed herein are the following: reads obtained by sequencing nucleic acids, the reference genome or sequence, thresholds for calling a test sample as either affected, non-affected, or no call, the actual calls of medical conditions related to a sequence of interest, diagnoses (clinical condition associated with the calls), recommendations for further tests derived from the calls and/or diagnoses, treatment and/or monitoring plans derived from the calls and/or diagnoses. In some embodiments, these various types of data are obtained, stored transmitted, analyzed, and/or manipulated at one or more locations using distinct apparatus. The processing options span a wide spectrum of options. At one end of the spectrum, all or much of this information is stored and used at the location where the test sample is processed, e.g., a doctor's office or other clinical setting. At the other end of the spectrum, the sample is obtained at one location, it is processed and optionally sequenced at a different location, reads are aligned and calls are made at one or more different locations, and diagnoses, recommendations, and/or plans are prepared at still another location (which may be a location where the sample was obtained).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

NA12878 genomic DNA was obtained from Coriell Institute (Coriell Institute, NA12878). The concentration was measured by Qubit dsDNA HS assay kit (Thermo Fisher Scientific, Q32851) and the amount of DNA used in library preparation was 10 ng. DNA substrates were diluted into 50 μl IDTE buffer (IDT, Nov. 5, 2001-09), and sheared into fragments of about 100-600 bp using a focused acoustic sonicator (Covaris, M220). The sonication parameters were set as follows: peak incident power 50W, duty factor 20%, cycle per burst 200, duration 150 seconds, and temperature 6-8° C. The size of the sheared DNA fragments was confirmed by LabChip GXII touch 24 (Perkin Elmer).

incubated beads with 150 μl of L-Desulphonation Buffer at room temperature (20-30° C.) for 25 minutes. The plates were placed on the magnetic stand for 3 minutes and supernatant discarded, followed by washing the beads with 300 μl of M-Wash Buffer twice. After the washing step, the plate was transferred to a metal heater (Illumina, SC-60-504, BD-60-601) at 55° C. for 30 minutes to dry the beads, then 16 μl of M-Elution Buffer was added with additional 4 min incubation at 55° C. The plate was then moved to the magnetic stand for 1 minute and the supernatant was recovered as template for subsequent library prep steps.

Figure 2:
FIG. 2 illustrates example adapters, in accordance with an embodiment. The illustration includes SEQ ID NOs: 4-7, in order from top to bottom.
Figure 3:
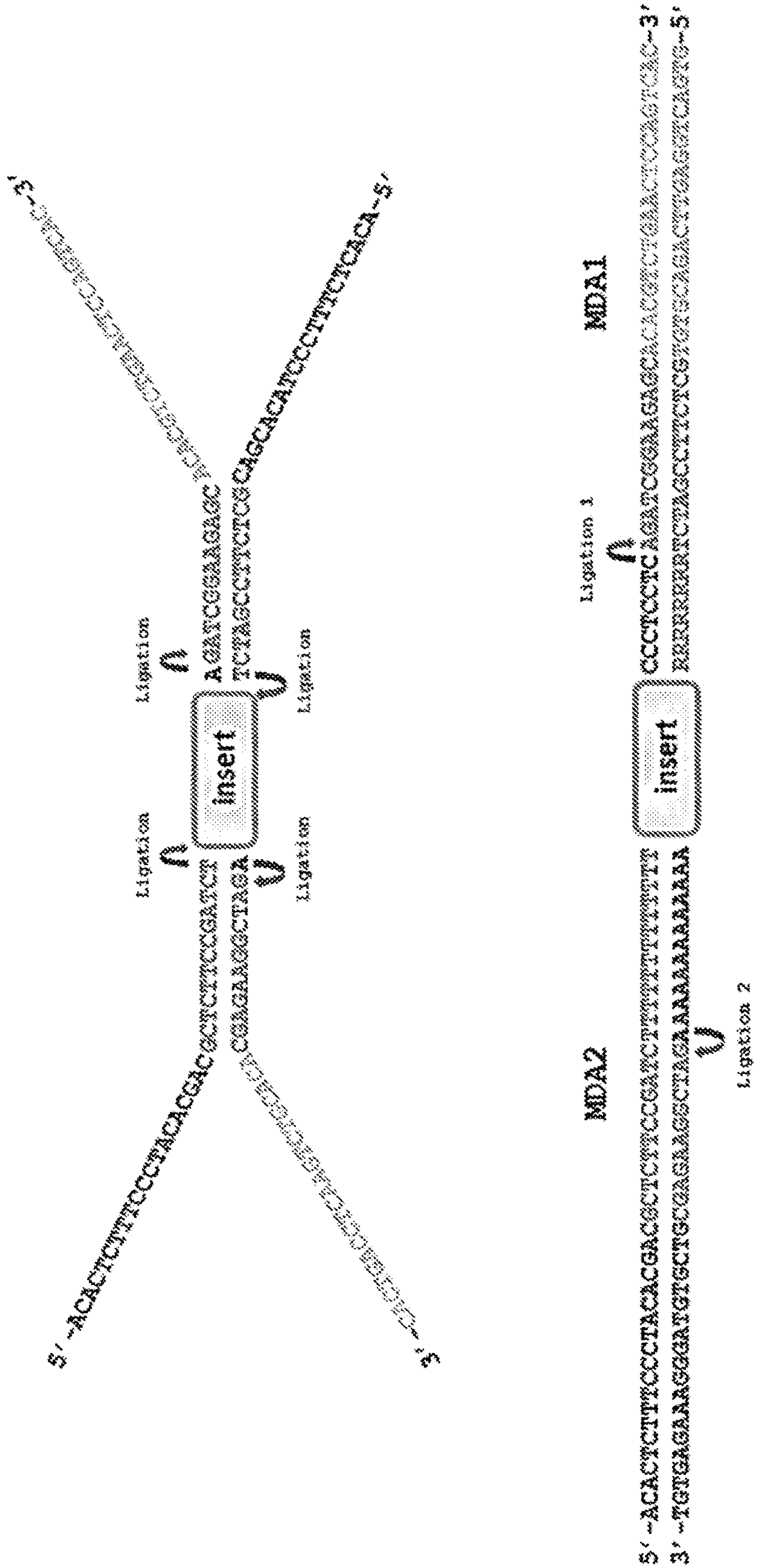
FIG. 3 illustrates a comparison between a polynucleotide prepared in accordance with an embodiment comprising a tailing reaction (bottom), and a polynucleotide prepared instead using "Y" adapters (top). The illustration includes SEQ ID NOs: 8-15, in order from left to right then top to bottom.

The splinter adapter MDA1 was designed to have a plurality of eight G or A randomly synthesized at 9:1 molar ratio. During the first tailing and ligation step, it annealed to the 3' end poly-C/T tail of the single stranded DNA substrate (as illustrated in FIG. 3, bottom). The sequences of the oligonucleotides forming MDA1 are illustrated in FIG. 2. The MDA1 adapter was prepared by annealing oligo ATN-R2-Top and ATN-R2-Bot together. In detail, 50 μl of each oligo (100 μM) was mixed and incubated at 95° C. for 10 minutes and allowed to slowly cool to room temperature in 10 mM Tris-HCl containing 0.1 mM EDTA and 50 mM NaCl. The 3' ends of both oligos were blocked by a phosphate group to prevent self-ligation. The MDA2 adapter was prepared with ATN-R1-Top and ATN-R1-Bot oligo following similar strategy. The sequences of the oligonucleotides forming MDA2 are also illustrated in FIG. 2. Sequences for oligonucleotides forming MDA1, MDA2, and for an amplification primer designated "Anchor primer" are set forth in Table 1.

TABLE 1

| Oligo | Sequence | Notes |
|---|---|---|
| ATN-R2-Top | AGATCGGAAGAGCACACGTCTGAACTCC AGTCAC (SEQ ID NO: 4) | 5' phosphate; 3' phosphate |
| ATN-R2-Bot | GTGACTGGAGTTCAGACGTGTGCTCTTCC GATCTRRRRRRRR (SEQ ID NO: 5) | 3' phosphate; R (G:A) = 9:1 premix |
| ATN-R1-Top | AGATCGGAAGAGCGTCGTGTAGGGAAAG AGTGT (SEQ ID NO: 6) | 5' phosphate; 3' phosphate |
| ATN-R1-Bot | ACACTCTTTCCCTACACGACGCTCTTCCG ATCTTTTTTTTTTTTT (SEQ ID NO: 7) | 3' phosphate |
| LAP (Anchor primer) | GTGACTGGAGTTCAGACGTGTGCTCTTCC GATC (SEQ ID NO: 16) | |

If not mentioned, all experiments were performed with two to three technical replicates.

The bisulfite conversion step (BC) was carried out with a modified protocol from EZ-96 DNA methylation-lightning™ MagPrep (Zymo, D5047). 97.5 μl of Lightning Conversion Reagent and 15 μl of sheared genomic DNA or cfDNA were added in a 48-well Plate (Thermo Fisher Scientific, AB0648). The samples were mixed by pipetting up and down and incubated in a thermal cycler with the following conditions: (i) 98° C. for 8 minutes; (ii) 54° C. for 60 minutes; (iii) 4° C. storage for up to 20 hours. The BC-treated DNA samples were transferred to a 96-well midi-plate (Thermo Scientific, AB0859) with preloaded 450 μl of M-Binding Buffer and 7.5 μl of MagBinding Beads for each well. Components were mixed thoroughly and the plate was allowed to stand at room temperature for 5 minutes. The plate was then transferred to a magnetic stand for an additional 5 minutes, and the supernatant was removed. The beads were washed with 300 μl of M-Wash Buffer and Bisulfite converted DNA fragments were end-repaired by mixing 12.5 μl of DNA sample, 1.5 μl of 10× CutSmart buffer (NEB, B7204S), 1 μl Shrimp alkaline phosphatase (NEB, M0371L), and incubated at 37° C. for 30 minutes. The products were further denatured by incubating at 95° C. for 5 min and fast cooling on ice.

Next, the first ligation reaction was performed in a 20 μl reaction volume containing pretreated DNA substrates, 1×CutSmart Buffer, 0.25 mM $CoCl_2$ (NEB, B0252S), 0.025 mM β-Nicotinamide adenine dinucleotide (NEB, B9007S), 0.09 mM dCTP (Roche, 11934520001), 0.01 mM dTTP (Roche, 11934546001), 1 μM MDA1 adapter, 0.5 U/μl *E. coli* ligase (NEB,M0205L) and 0.5 U/μl terminal deoxynucleotidyl transferase (TdT; NEB, M0315S). The reaction was incubated at 37° C. for 30 minutes followed by heating at 95° C. for 2 minutes and held at 4° C.

The ligated product was extended and linearly amplified in the presence of 1X KAPA HiFi HotStart Uracil+ReadyMix (KAPA, KK2802), and 0.91 μM anchor primer. The linear amplification reaction was carried out with the following thermal profile: (i) 95° C. for 5 minutes; (ii) 98° C. for 20 seconds, 62° C. for 30 seconds, 72° C. for 1 minutes, 15 cycles and (iii) 72° C. for 5 minutes. After the reaction was completed, buffer was exchanged by purification with 2.5X AMPure XP beads (Beckman Coulter, A63881) and eluted with 11.5 μl Elution Buffer (10 mM Tris-HCl, pH 8.0).

The second ligation reaction was performed in a 20 μl reaction volume containing 10 μl of purified DNA products, 1X CutSmart buffer, 0.25 mM $CoCl_2$ (NEB, B0252S), 0.025 mM B-Nicotinamide adenine dinucleotide (NEB, B9007S), 0.1 mM dATP (Roche, 11934511001), 1 μM MDA2, 0.5 U/μl *E. coli* ligase (NEB,M0205L) and 0.5 U/μl terminal deoxynucleotidyl transferase (NEB, M0315S). The reaction was incubated at 37° C. for 30 minutes followed by heating at 95° C. for 2 minutes and held at 4° C. An illustration of an example product of the second ligation is provided in FIG. 3 (bottom), compared to the product of a ligation reaction involving "Y" adapters (top).

PCR enrichment of ligated product was performed in a 50 μl reaction containing 20 μl of the above-mentioned DNA product, 1X KAPA HiFi buffer, dNTP, 1 μM primer F and primer R, and 1 u/μl KAPA HiFi polymerase. The PCR program was as follows: (i) 95° C. for 5 minutes; (ii) 98° C. for 20 seconds, 60° C. for 30 seconds, 72° C. for 1 minutes, 12 cycles and (iii) 72° C. for 10 minutes. The PCR products were purified using Agencourt AMPure XP beads (Beckman Coulter, A63881) and eluted in 18 μl of EB (10 mM Tris-HCl, pH 8.0). The sequence of primer F was ACACTCTTTCCCTACACGACGCTCTTCCGATCT (SEQ ID NO: 17). The sequence of primer R was GTGACTGGAGTTCAGACGTGTGCTCTTCCGATC (SEQ ID NO: 18).

15 μl of purified DNA library (50-200 ng/μl) was mixed well with 4 μl blocker mix, and incubated in a thermal cycler with the following conditions: (i) 95° C. for 5 minutes; (ii) 65° C. hold. Meanwhile 10 μl of Hybridization Buffer (13×SSPE; 13.5 mM EDTA; 13×Denhart's Solution; 0.45% SDS), 0.5 μl RNAse-inhibitor, and 0.5 μl Agilent SureSelect Custom Panel Probe Pool were pre-warmed at 65° C. for 2 minutes. Then the entire contents of the DNA-blocker mix were transferred to the probe mix, allowing the hybridization reaction to proceed at 65° C. for 16-24 hours.

Figure 4:
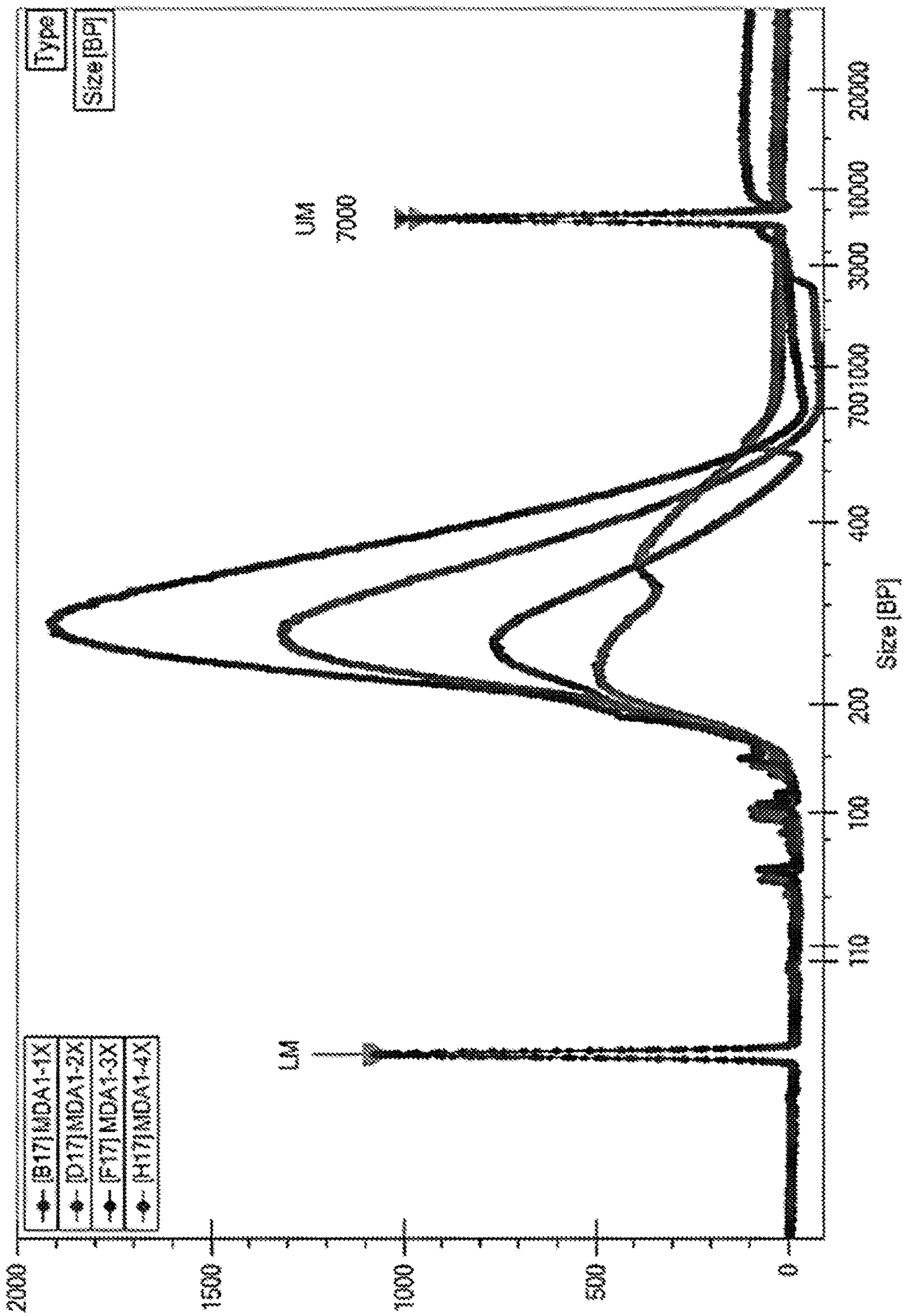
FIG. 4 illustrates an example plot of a capillary electrophoretic analysis.

FIG. 4 illustrates an example plot of a capillary electrophoretic analysis, showing an example size distribution of pre-capture library fragments after PCR enrichment. The expected peak size was 200-400 bp. All libraries were loaded on HT DNA High Sensitivity LabChip Kit (Perkin Elmer). The highest curve at 300 bp shows the ligated substrate when provided with 1x MDA1 adapters. The next curves, from top to bottom, represent 2x, 3x, and 4x adapters, respectively. The data indicate that 1x MDA1 is sufficient for attaching the adaptor, and the ligation efficiency decreased with increasing MDA1 concentration, under these conditions.

After the hybridization, 25 μl of streptavidin-conjugated DynaBeads™ (Thermo Fisher Scientific, 65602) were conditioned by washing with 200 μl Binding Buffer (10 mM Tris-HCl pH 8.0, 0.5 mM EDTA, 1 M NaCl) for four times. DNA capture was performed at 25° C. in a thermomixer for 30 minutes at 600 RPM. To remove the non-target DNA pulled down via non-specific binding, the beads were first washed once at room temperature with 500 μl of Wash Buffer1, then three times with Wash Buffer2 (10 mM Tris-HCl pH 8.0, 0.02% Triton X-100) at 65° C. The beads were then resuspended in 20 μl of elution buffer (10 mM Tris-HCl, pH 8.0) and used as template for the following indexing PCR step.

For multiplex sequencing, 5 μl indexing primers (premixed i5 and i7, 20 μM each) were added in a 50 μl reaction containing 20 μl resuspended T1 beads, and 25 μl Kapa HiFi hot start ready mix (Kapa Biosystem, KK2602). The PCR Program was as follows: (i) 98° C. for 45 seconds; (ii) 98° C. for 15 seconds, 60° C. for 30 seconds, 72° C. for 1 minute, 12 cycles and (iii) 72° C. for 5 minutes. Purified DNA libraries were eluted in 20 μl of EB and quantified by Qubit dsDNA HS assay kit. The sequence of index primer i5 was AATGATACGGCGACCACCGAGATCTACACGT-TAGTTCACACTCTTTCCCTACACGAC G (SEQ ID NO: 19; with the underlined sequence corresponding to an example index sequence). The sequence of index primer i7 was CAAGCAGAAGACGGCATACGAGATGT-GATGCCGTGACTGGAGTTCAGACGTG (SEQ ID NO: 20; with the underlined sequence corresponding to an example index sequence).

The products of the indexing PCR step were sequenced on an Illumina HiSeq 2500 or NovaSeq using PE150 cycle runs according to the manufacturer's instructions. FASTQ sequences were de-multiplexed by analytical pipeline, and general library quality metrics were analyzed. Illustrative library bioinformatics QC summary tables are shown in Tables 2A and 2B below.

TABLE 2A

| Sample Name | Input DNA (ng) | Total PF Reads | Mapped Ratio | Insert Size |
|---|---|---|---|---|
| MDA1-1X | 10 | 8,666,046 | 95.79% | 188 |
| MDA1-2X | 10 | 7,577,663 | 95.87% | 187 |
| MDA1-3X | 10 | 8,150,850 | 96.12% | 187 |
| MDA1-4X | 10 | 8,851,169 | 96.01% | 189 |

TABLE 2B

| Sample Name | Covered Complexity | On Target % | Deduped Median Coverage | Pre-deduped median Coverage | Uniformity (0.2 × mean) |
|---|---|---|---|---|---|
| MDA1-1X | 65.26% | 64.16% | 366 | 537 | 96.40% |
| MDA1-2X | 64.45% | 65.43% | 323 | 478 | 96.30% |
| MDA1-3X | 59.59% | 68.02% | 337 | 537 | 96.20% |
| MDA1-4X | 52.65% | 67.63% | 324 | 580 | 96.30% |

An overview illustration of an example library preparation method is provided in FIG. 1. A tailing step is performed using TdT with appropriate dNTP(s) to create a homopolymer or near-homopolymer tail to the 3' end of ssDNA fragments. The homopolymer anneals to the 3' overhang of an adapter containing a 5' phosphate group in the top strand. The ligation reaction catalyzed by ligase seals the 3' end of the ssDNA fragment to prevent excessive tailing. The bottom strand of the adapter is competed out by the anchor primer, exposing the initiating sites for a linear amplification process. The amplified ssDNA strands serve as templates for the second round of tailing and ligation, the products of which are then amplified.

Example 2

NA12878 genomic DNA was obtained from Coriell Institute (Coriell Institute, NA12878). The concentration was measured by Qubit dsDNA HS assay kit (Thermo Fisher Scientific, Q32851) and the amount of DNA used in library preparation ranged from 2-30 ng. DNA substrates were diluted into 50 μl IDTE buffer (IDT, Nov. 5, 2001-09), and sheared into fragments of about 100-600 bp using a focused acoustic sonicator (Covaris, M220). The sonication parameters were set as follows: peak incident power 50W, duty factor 20%, cycle per burst 200, duration 150 seconds, and temperature 6-8° C. The size of the sheared DNA fragments was confirmed by LabChip GXII touch 24 (Perkin Elmer).

Plasma samples were obtained from human blood draws. Cell free DNA (cfDNA) was extracted using the QiaAmp Circulating Nucleic Acid Kit (Qiagen, 55114). cfDNA was quantified by Qubit dsDNA HS assay kit as NA12878 genomic DNA but not subjected to fragmentation.

If not mentioned, all experiments were performed with two to three technical replicates.

The bisulfite conversion step (BC) was carried out with a modified protocol from EZ-96 DNA methylation-lightning™ MagPrep (Zymo, D5047). 97.5 μl of Lightning Conversion Reagent and 15 μl of sheared genomic DNA or cfDNA were added in a 48-well Plate (Thermo Fisher Scientific, AB0648). The samples were mixed by pipetting up and down and incubated in a thermal cycler with the following conditions: (i) 98° C. for 8 minutes; (ii) 54° C. for 60 minutes; (iii) 4° C. storage for up to 20 hours. The BC-treated DNA samples were transferred to a 96-well midi-plate (Thermo Scientific, AB0859) with preloaded 450 μl of M-Binding Buffer and 7.5 μl of MagBinding Beads for each well. Components were mixed thoroughly and the plate was allowed to stand at room temperature for 5 minutes. The plate was then transferred to a magnetic stand for an additional 5 minutes, and the supernatant was removed. The beads were washed with 300 μl of M-Wash Buffer and incubated beads with 150 μl of L-Desulphonation Buffer at room temperature (20-30° C.) for 25 minutes. The plates were placed on the magnetic stand for 3 minutes and supernatant discarded, followed by washing the beads with 300 μl of M-Wash Buffer twice. After the washing step, the plate was transferred to a metal heater (Illumina, SC-60-504, BD-60-601) at 55° C. for 30 minutes to dry the beads, then 16 μl of M-Elution Buffer was added with additional 4 min incubation at 55° C. The plate was then moved to the magnetic stand for 1 minute and the supernatant was recovered as template for subsequent library prep steps.

The splinter adapter MDA1 was designed to have a plurality of eight G or A randomly synthesized at 9:1 molar ratio. During the first tailing and ligation step, it annealed to the 3' end poly-C/T tail of the single stranded DNA substrate (as illustrated in FIG. 3, bottom). The sequences of the oligonucleotides forming MDA1 are illustrated in FIG. 2. The MDA1 and MDA2 adapters were prepared as in Example 1. Sequences for oligonucleotides forming MDA1, MDA2, and for an amplification primer designated "Anchor primer" are set forth in Table 1, above.

Bisulfite converted DNA fragments were end-repaired by mixing 12.5 μl of DNA sample, 1.5 μl of 10× CutSmart buffer (NEB, B7204S), 1 μl Shrimp alkaline phosphatase (NEB, M0371L), and incubated at 37° C. for 30 minutes. The products were further denatured by incubating at 95° C. for 5 min and fast cooling on ice.

Next, the first ligation reaction was performed in a 20 μl reaction volume containing pretreated DNA substrates, 1×CutSmart Buffer, 0.25 mM $CoCl_2$ (NEB, B0252S), 0.025 mM β-Nicotinamide adenine dinucleotide (NEB, B9007S), 0.09 mM dCTP (Roche, 11934520001), 0.01 mM dTTP (Roche, 11934546001), 1 μM MDA1 adapter, 0.5 U/μl *E. coli* ligase (NEB, M0205L) and 0.5 U/μl terminal deoxynucleotidyl transferase (TdT, NEB, M0315S). The reaction was incubated at 37° C. for 30 minutes followed by heating at 95° C. for 2 minutes and held at 4° C.

The ligated product was extended and linearly amplified in the presence of 1X KAPA HiFi HotStart Uracil+ReadyMix (KAPA, KK2802), and 0.91 μM anchor primer. The linear amplification reaction was carried out with the following thermal profile: (i) 95° C. for 5 minutes; (ii) 98° C. for 20 seconds, 62° C. for 30 seconds, 72° C. for 1 minutes, 15 cycles and (iii) 72° C. for 5 minutes. After the reaction was completed, buffer was exchanged by purification with 2.5X AMPure XP beads (Beckman Coulter, A63881) and eluted with 11.5 μl Elution Buffer (10 mM Tris-HCl, pH 8.0).

The second ligation reaction was performed in a 20 μl reaction volume containing 10 μl of purified DNA products, 1X CutSmart buffer, 0.25 mM $CoCl_2$ (NEB, B0252S), 0.025 mM B-Nicotinamide adenine dinucleotide (NEB, B9007S), 0.1 mM dATP (Roche, 11934511001), 1 μM MDA2, 0.5 U/μl *E. coli* ligase (NEB,M0205L) and 0.5 U/μl terminal deoxynucleotidyl transferase (NEB, M0315S). The reaction was incubated at 37° C. for 30 minutes followed by heating at 95° C. for 2 minutes and held at 4° C. An illustration of an example product of the second ligation is provided in FIG. 3 (bottom), compared to the product of a ligation reaction involving "Y" adapters (top).

PCR enrichment of ligated product was performed in a 50 μl reaction containing 20 μl of the above-mentioned DNA product, 1X KAPA HiFi buffer, dNTP, 1 μM primer F and primer R, and 1 U/μl KAPA HiFi polymerase. The PCR program was as follows: (i) 95° C. for 5 minutes; (ii) 98° C. for 20 seconds, 60° C. for 30 seconds, 72° C. for 1 minutes, 12 cycles and (iii) 72° C. for 10 minutes. The PCR products were purified using Agencourt AMPure XP beads (Beckman Coulter, A63881) and eluted in 18 μl of EB (10 mM Tris-HCl, pH 8.0).

Figure 5A:
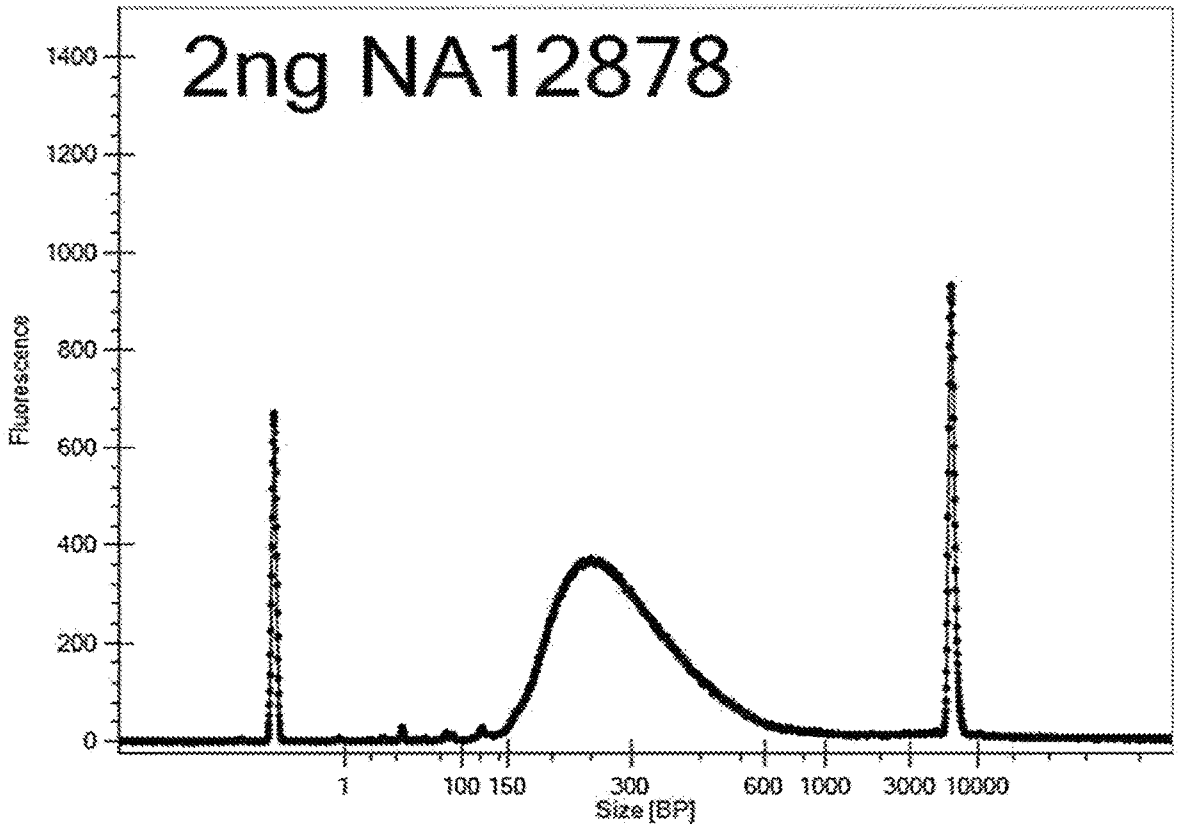
FIGS. 5A-C illustrate example plots of capillary electrophoretic analyses.
Figure 5A:
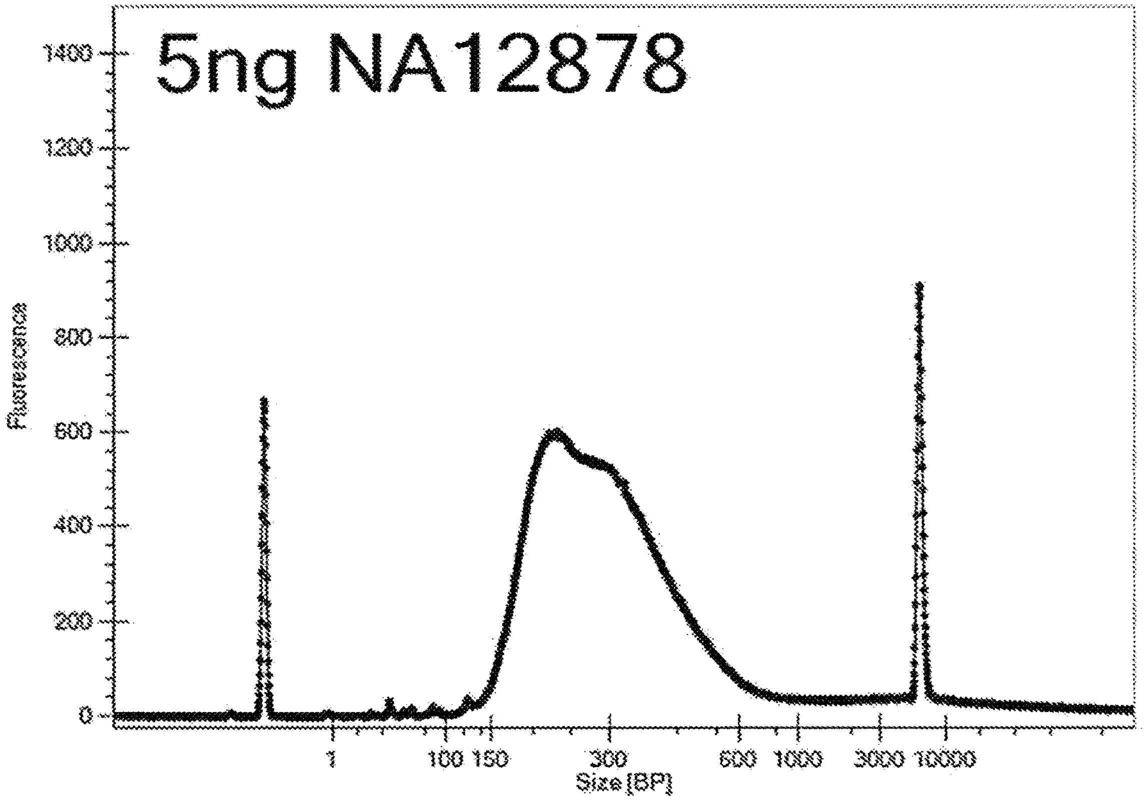
Figure 5B:
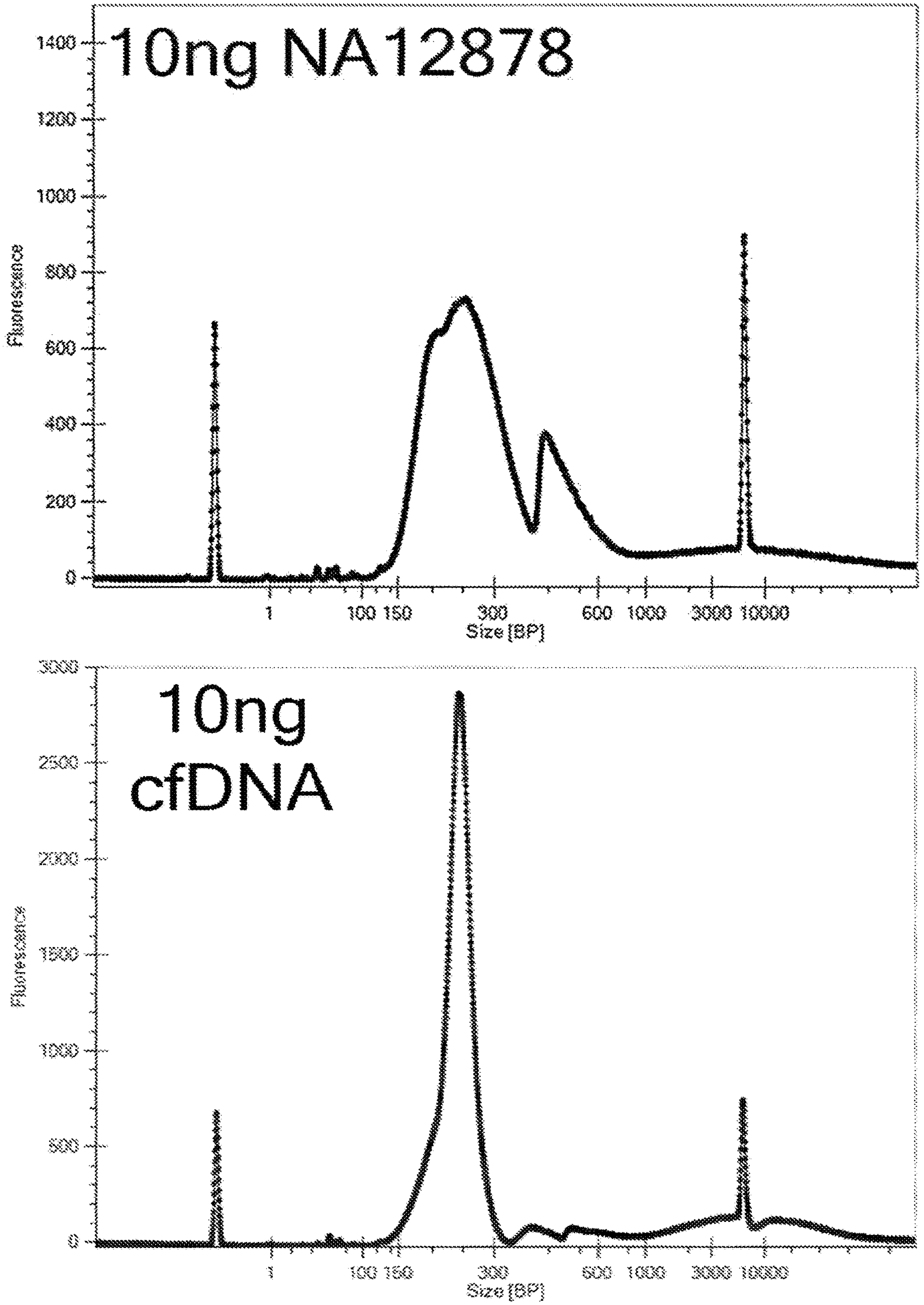
Figure 5C:
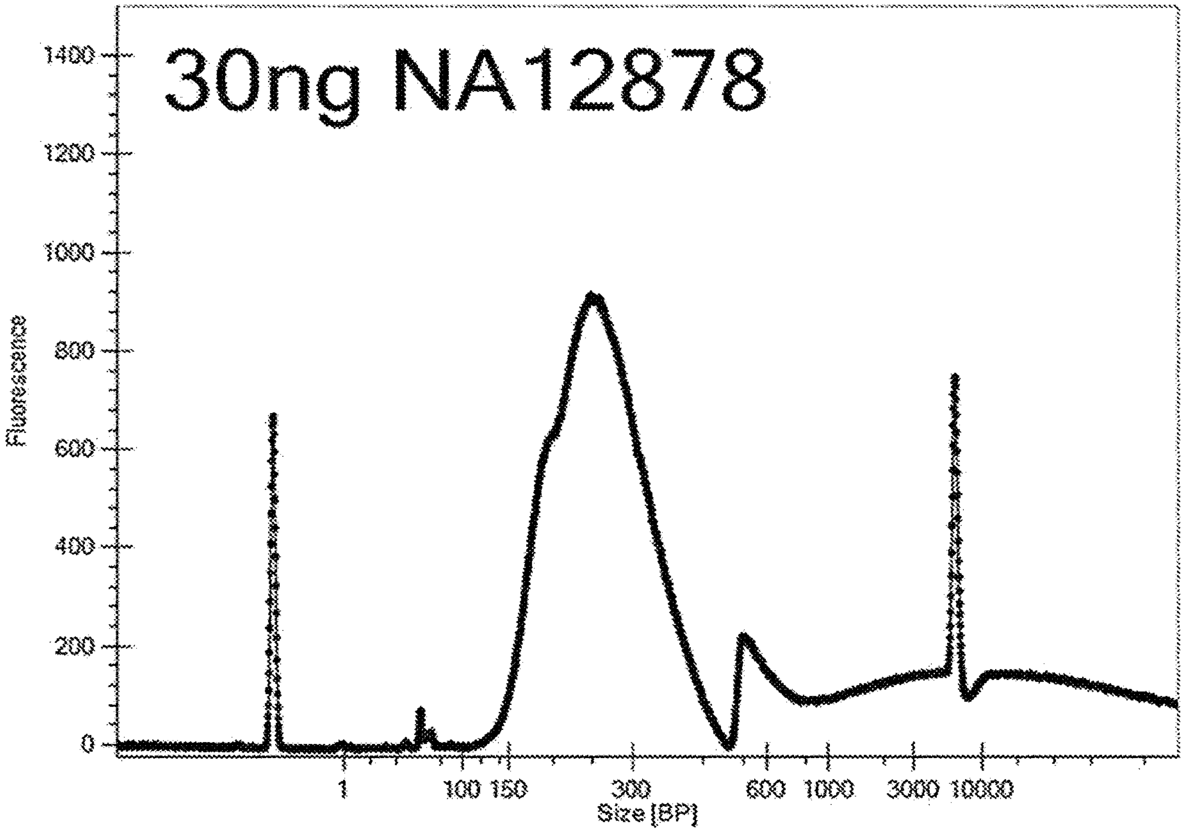

FIGS. 5A-C illustrate example plots of a capillary electrophoretic analyses, showing example size distributions of pre-capture library fragments after PCR enrichment. The expected peak size was 200-400 bp. The pre-captured library yield increased as input increased. At 10 ng of input, the cfDNA had a higher yield than the sheared genomic DNA (gDNA). All libraries were loaded on HT DNA High Sensitivity LabChip Kit (Perkin Elmer).

15 μl of purified DNA library (50-200 ng/μl) was mixed well with 4 μl blocker mix and incubated in a thermal cycler with the following conditions: (i) 95° C. for 5 minutes; (ii) 65° C. hold. Meanwhile 10 μl of Hybridization Buffer (13×SSPE; 13.5 mM EDTA; 13×Denhart's Solution; 0.45% SDS), 0.5 μl RNAse-inhibitor, and 0.5 μl Agilent SureSelect Custom Panel Probe Pool were pre-warmed at 65° C. for 2 minutes. Then the entire contents of the DNA-blocker mix were transferred to the probe mix, allowing the hybridization reaction to proceed at 65° C. for 16-24 hours.

After the hybridization, 25 μl of streptavidin-conjugated DynaBeads™ (Thermo Fisher Scientific, 65602) were conditioned by washing with 200 μl Binding Buffer (10 mM Tris-HCl pH 8.0, 0.5 mM EDTA, 1 M NaCl) for four times. DNA capture was performed at 25° C. in a thermomixer for 30 minutes at 600 RPM. To remove the non-target DNA pulled down via non-specific binding, the beads were first washed once at room temperature with 500 μl of Wash Buffer1 (0.15 M Sodium Chloride, 0.015 M Sodium Citrate, 0.1% SDS), then three times with Wash Buffer2 (0.015 M Sodium Chloride, 0.0015 M Sodium Citrate, 0.1% SDS) at 65° C. The beads were then resuspended in 20 μl of elution buffer (10 mM Tris-HCl, pH 8.0) and used as template for the following indexing PCR step.

For multiplex sequencing, 5 μl indexing primers (pre-mixed i5 and i7, 20 μM each) were added in a 50 μl reaction containing 20 μl resuspended T1 beads, and 25 μl Kapa HiFi hotstart ready mix (Kapa Biosystem, KK2602). The PCR Program was as follows: (i) 95° C. for 5 minutes; (ii) 98° C. for 20 seconds, 60° C. for 30 seconds, 72° C. for 1 minute, 12 cycles and (iii) 72° C. for 10 minutes. Purified DNA libraries were eluted in 20 μl of EB and quantified by Qubit dsDNA HS assay kit.

The products of the indexing PCR step were sequenced on an Illumina HiSeq 2500 or NovaSeq using PE150 cycle runs according to the manufacturer's instructions. FASTQ sequences were de-multiplexed by analytical pipeline, and general library quality metrics were analyzed. Illustrative library bioinformatics QC summary tables are shown in Tables 3A and 3B below.

TABLE 3A

| Sample Name | Specimen | Input DNA (ng) | Total PF Reads | Mapped Ratio | Insert Size |
|---|---|---|---|---|---|
| 2ng-12878-1 | NA12878 genomic DNA | 2 | 1.42E+07 | 97.34% | 184 |
| 2ng-12878-2 | NA12878 genomic DNA | 2 | 1.39E+07 | 97.69% | 184 |
| 5ng-12878-1 | NA12878 genomic DNA | 5 | 1.36E+07 | 97.89% | 183 |
| 5ng-12878-2 | NA12878 genomic DNA | 5 | 1.36E+07 | 97.70% | 184 |
| 10ng-12878-1 | NA12878 genomic DNA | 10 | 1.35E+07 | 97.87% | 179 |
| 10ng-12878-2 | NA12878 genomic DNA | 10 | 1.35E+07 | 98.15% | 186 |
| 30ng-12878-1 | NA12878 genomic DNA | 30 | 1.37E+07 | 98.24% | 194 |
| 30ng-12878-2 | NA12878 genomic DNA | 30 | 1.37E+07 | 98.14% | 193 |
| 10ng-PLA-1 | cfDNA | 10 | 1.56E+07 | 98.45% | 163 |
| 10ng-PLA-2 | cfDNA | 10 | 1.54E+07 | 98.50% | 163 |

TABLE 3B

| Sample Name | On Target % | Deduped Median Coverage | Pre-deduped median Coverage | Coverage Uniformity (>0.2 × mean) |
|---|---|---|---|---|
| 2ng-12878-1 | 79.02% | 291 | 984 | 95.60% |
| 2ng-12878-2 | 80.32% | 300 | 985 | 95.60% |
| 5ng-12878-1 | 79.59% | 472 | 989 | 96.20% |
| 5ng-12878-2 | 80.25% | 475 | 987 | 96.30% |
| 10ng-12878-1 | 80.94% | 603 | 992 | 95.80% |
| 10ng-12878-2 | 80.77% | 600 | 991 | 96.40% |
| 30ng-12878-1 | 80.25% | 750 | 991 | 96.70% |
| 30ng-12878-2 | 80.13% | 745 | 989 | 96.70% |
| 10ng-PLA-1 | 82.81% | 620 | 991 | 93.30% |
| 10ng-PLA-2 | 82.98% | 634 | 990 | 93.40% |

Example 3

SW48 genomic DNA, which has increased levels of methylation, was purchased from ATCC (ATCC, CCL231). The concentration was measured by Qubit dsDNA HS assay kit (Thermo Fisher Scientific, Q32851). 10 ng of SW48 gnomic DNA was whole genome amplified (WGA) by REPLI-g Mini Kit (Qiagen 150023) in 50 μl following standard protocol (including 16 hour incubation at 30° C.). The amplified material was purified by 100 μl Ampure XP bead (Beckman Coulter, A63881) and eluted into 50 μl IDTE buffer (IDT, Nov. 5, 2001-09). The final WGA DNA yield was about 3 μg with a methylation level of about 1/300 of original SW48. The WGA DNA was proportionally mixed with original SW48 genomic DNA at 0%, 20%, 50%, 80%, and 100% level to mimic genome-wide methylation level gradient. 50 ng of each DNA mix was sheared into fragments of about 100-600 bp using a focused acoustic sonicator (Covaris, M220). The sonication parameters were set as follows: peak incident power 50W, duty factor 20%, cycle per burst 200, duration 150 seconds, and temperature 6-8° C. The size of the sheared DNA fragments was confirmed by LabChip GXII touch 24 (Perkin Elmer).

The bisulfite conversion step (BC) was carried out with a modified protocol from EZ-96 DNA methylation-lightning™ MagPrep (Zymo, D5047). 97.5 μl of Lightning Conversion Reagent and 40 ng sheared genomic DNA mix in 15 μl were added in a 48-well Plate (Thermo Fisher Scientific, AB0648). The samples were mixed by pipetting up and down and incubated in a thermal cycler with the following conditions: (i) 98° C. for 8 minutes; (ii) 54° C. for 60 minutes; (iii) 4° C. storage for up to 20 hours. The BC-treated DNA samples were transferred to a 96-well midi-plate (Thermo Scientific, AB0859) with preloaded 450 μl of M-Binding Buffer and 7.5 μl of MagBinding Beads for each well. Components were mixed thoroughly and the plate was allowed to stand at room temperature for 5 minutes. The plate was then transferred to a magnetic stand for an additional 5 minutes, and the supernatant was removed. The beads were washed with 300 μl of M-Wash Buffer and incubated beads with 150 μl of L-Desulphonation Buffer at room temperature (20-30° C.) for 25 minutes. The plates were placed on the magnetic stand for 3 minutes and supernatant discarded, followed by washing the beads with 300 μl of M-Wash Buffer twice. After the washing step, the plate was transferred to a metal heater (Illumina, SC-60-504, BD-60-601) at 55° C. for 30 minutes to dry the beads, then 16 μl of M-Elution Buffer was added with additional 4 min incubation at 55° C. The plate was then moved to the magnetic stand for 1 minute and the supernatant was recovered as template for subsequent library prep steps.

The MDA1 and MDA2 adapters were prepared as in Example 1. Sequences for oligonucleotides forming MDA1, MDA2, and for an amplification primer designated "Anchor primer" are set forth in Table 1, above.

10 ng of each bisulfite converted DNA fragments were end-repaired by mixing 12.5 μl of DNA sample, 1.5 μl of 10x CutSmart buffer (NEB, B7204S), 1 μl Shrimp alkaline phosphatase (NEB, M0371L), and incubated at 37° C. for 30 minutes. The products were further denatured by incubating at 95° C. for 5 min and fast cooling on ice.

The first ligation, subsequent amplification, second ligation, and PCR enrichment were performed as in Example 1. 15 μl of purified DNA library (50-200 ng/μl) was mixed well with 4 μl blocker mix, and incubated in a thermal cycler with the following conditions: (i) 95° C. for 5 minutes; (ii) 65° C. hold. Meanwhile 10 μl of Hybridization Buffer (13×SSPE; 13.5 mM EDTA; 13×Denhart's Solution; 0.45% SDS), 0.5 μl RNAse-inhibitor, and 0.5 μl Agilent SureSelect Custom Panel Probe Pool were pre-warmed at 65° C. for 2 minutes. Then the entire contents of the DNA-blocker mix was transferred to the probe mix, allowing the hybridization reaction to proceed at 65° C. for 16-24 hours.

Figure 6A:
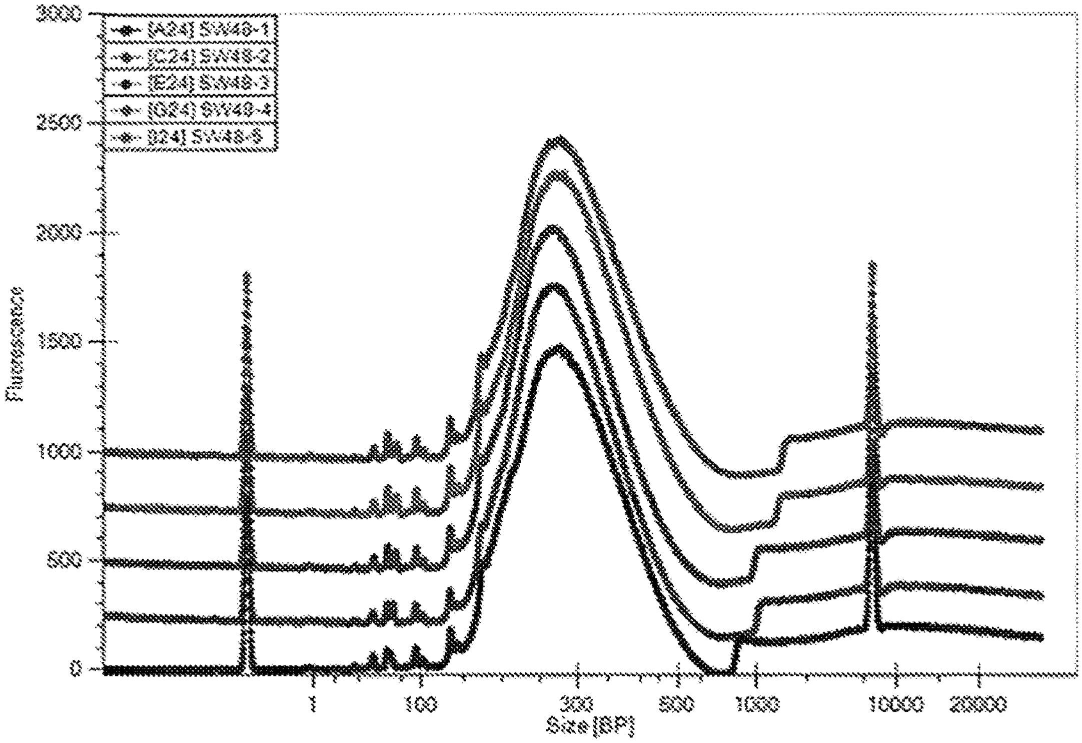
FIGS. 6A-B illustrate example plots of electrophoretic analyses

FIG. 6A illustrates an example plot of a capillary electrophoretic analysis, showing size distribution of pre-capture library fragments after PCR enrichment. Curves from top to bottom correspond to samples indicated in the legend from bottom to top. The expected peak size was 200-400 bp. All libraries were loaded on HT DNA High Sensitivity LabChip Kit (Perkin Elmer). All pre-captured libraries have very similar yield and insert size, indicating that the library prep method had no bias on methylated states.

Figure 6B:
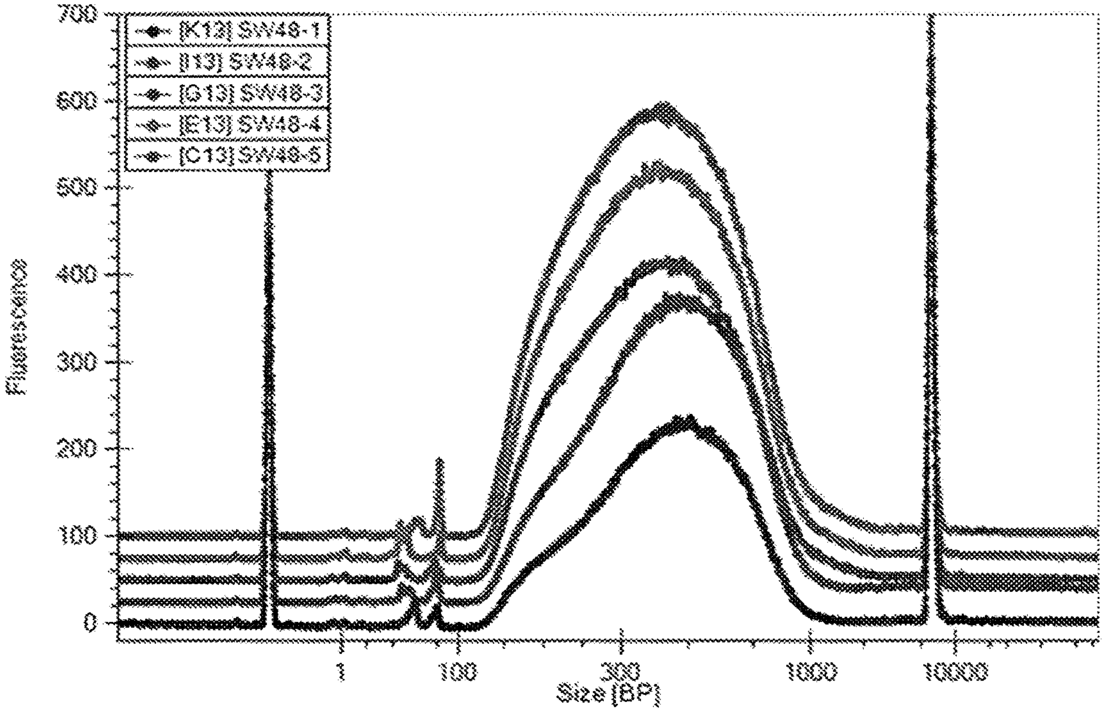

DNA was captured using streptavidin-conjugated DynaBeads™, eluted, and amplified using indexing primers as in Example 1. FIG. 6B illustrates an example plot of a capillary electrophoretic analysis, showing size distribution of post-capture library fragments after indexing PCR. All libraries were loaded on HT DNA High Sensitivity LabChip Kit (Perkin Elmer). Library yield gradually decreased as the original methylation level increased, indicating the general GC bias of the library preparation procedure under these conditions.

The products of the indexing PCR step were sequenced on an Illumina HiSeq 2500 using PE150 cycle runs according to the manufacturer's instructions. FASTQ sequences were de-multiplexed by analytical pipeline, and general library quality metrics were analyzed. Illustrative library bioinformatics QC summary tables are shown in Tables 4A and 4B below.

TABLE 4A

| Sample Name | % SW48 DNA | % WGA DNA | Input DNA (ng) | PF Read | Mapped Ratio |
|---|---|---|---|---|---|
| SW48-1 | 100 | 0 | 10 | 8.26E+06 | 99.2% |
| SW48-2 | 80 | 20 | 10 | 8.96E+06 | 99.0% |
| SW48-3 | 50 | 50 | 10 | 8.04E+06 | 98.7% |
| SW48-4 | 20 | 80 | 10 | 7.61E+06 | 97.6% |
| SW48-5 | 0 | 100 | 10 | 6.88E+06 | 97.5% |

TABLE 4B

| Sample Name | Covered Complexity | On Target % | Deduped Median Coverage | Pre-deduped median Coverage | Uniformity (0.2 × mean) |
|---|---|---|---|---|---|
| SW48-1 | 62% | 68.5% | 324 | 502 | 0.97 |
| SW48-2 | 65% | 64.9% | 348 | 510 | 0.974 |
| SW48-3 | 68% | 61.1% | 288 | 408 | 0.97 |
| SW48-4 | 80% | 34.2% | 160 | 194 | 0.971 |
| SW48-5 | 81% | 33.7% | 140 | 168 | 0.953 |

Figure 7:
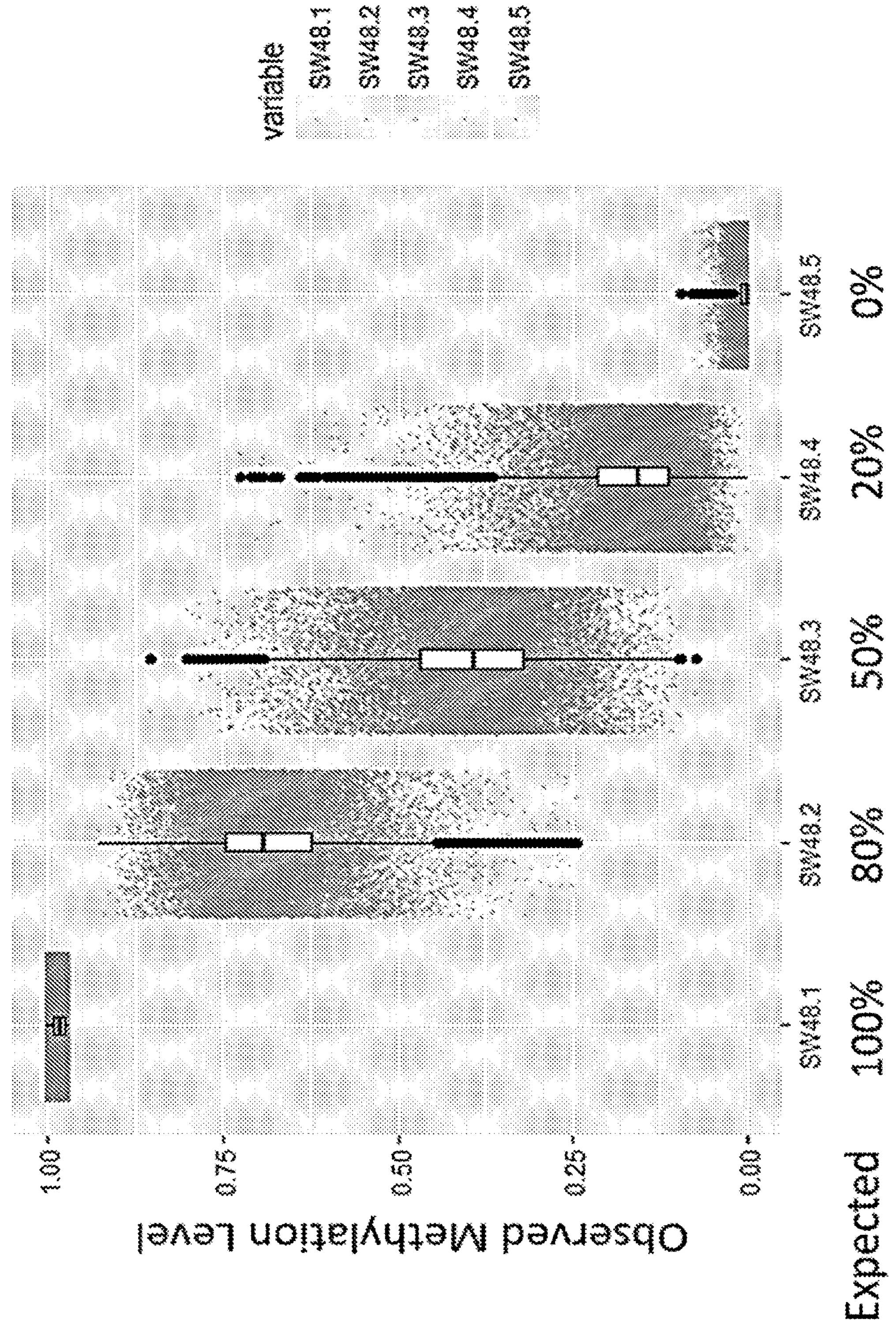
FIG. 7 illustrates the methylation level of 12,977 targeted CpG sites across different samples.

Each targeted CpG methylation level was calculated based on alignment results and base count. FIG. 7 illustrates the methylation level of 12,977 targeted CpG sites. These sites have >97% methylation level in SW48-1 samples (100% SW48, 0% WGA). With different WGA sample spike-in, the methylation levels of these sites decreased proportionally and were within expectations. This indicated that the whole library preparation and capture process can precisely and accurately measure CpG methylation levels.

Example 4

NA12878 genomic DNA and customized 5% mutation genomic DNA reference were obtained from Coriell Institute (Coriell Institute, NA12878) and Horizon Discovery (HD-C669). The concentration was measured by Qubit dsDNA HS assay kit (Thermo Fisher Scientific, Q32851). The HD-C669 was proportionally mixed with NA12878 at a ratio of 1:9 to expect a mutation allele frequencies of 0.5% (the resulting mixture was named "PC1"). Mutations and their expected frequencies are listed in Table 6A. 50 ng of pure NA12878 and 0.5% AF Mixed DNA substrates were diluted into 50 µl IDTE buffer (IDT, Nov. 5, 2001-09), and sheared into fragments of about 100-600 bp using a focused acoustic sonicator (Covaris, M220). The sonication parameters were set as follows: peak incident power 50W, duty factor 20%, cycle per burst 200, duration 150 seconds, and temperature 6-8° C. The size of the sheared DNA fragments was confirmed by LabChip GXII touch 24 (Perkin Elmer). The sheared materials were quantified by Qubit dsDNA HS assay kit to get 10 ng as the library prep input.

If not mentioned, all experiments were performed with two to three technical replicates.

For reference, a library was prepared using a typical "Y" adapter procedure. 10 ng of sheared genomic DNA in 50 µl IDTE was added in a 48-well Plate (Thermo Fisher Scientific, AB0648). The samples were end repaired and ligated using standard KAPA Hyper Prep kit (KAPA Biosystem, KK8504). The "Y" adapters described in FIG. 3 (top) were used in the ligation system with final concentration at 0.8 µM.

For splinter adapter assisted library prep, 10 ng of sheared genomic DNA in 12.5 µl IDTE was added in a 48-well Plate (Thermo Fisher Scientific, AB0648) and end-repaired by mixing with 1.5 µl of 10× CutSmart buffer (NEB, B7204S) and 1 µl Shrimp alkaline phosphatase (NEB, M0371L). The mixture was incubated at 37° C. for 30 minutes and then heated to 95° C. for 5 min following fast cooling on ice. The MDA1 and MDA2 adapters were prepared as in Example 1. Sequences for oligonucleotides forming MDA1, MDA2, and for an amplification primer designated "Anchor primer" are set forth in Table 1, above. The first ligation, subsequent amplification, second ligation, and PCR enrichment were performed as in Example 1.

PCR enrichment of ligated products using both "Y" adapters and splinter adapters was performed in 50 µl reactions containing 20 µl of DNA product, 1X KAPA HiFi buffer, dNTP, 1 µM primer F and primer R, and 1 U/µl KAPA HiFi polymerase. The PCR program was as follows: (i) 95° C. for 5 minutes; (ii) 98° C. for 20 seconds, 60° C. for 30 seconds, 72° C. for 1 minutes, 12 cycles and (iii) 72° C. for 10 minutes. The PCR products were purified using Agencourt AMPure XP beads (Beckman Coulter, A63881) and eluted in 18 µl of EB (10 mM Tris-HCl, pH 8.0).

Figure 8A:
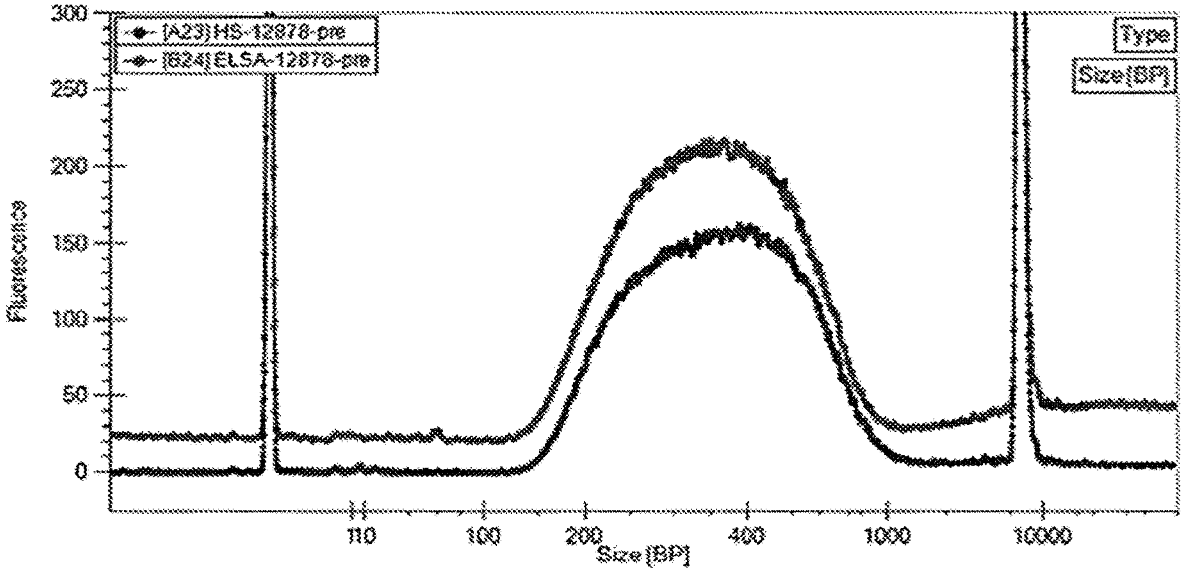
FIGS. 8A-B illustrate example plots of capillary electrophoretic analyses.

FIG. 8A illustrates an example plot of a capillary electrophoretic analysis, showing an example size distribution of pre-capture library fragments after PCR enrichment (top and bottom plots are ELSA-12878-pre and HS-12878-pre, respectively. "ELSA" denotes splinter adapter libraries and "HS" denotes "Y" adapter libraries.). The expected peak size was 200-500 bp. All libraries were loaded on HT DNA High Sensitivity LabChip Kit (Perkin Elmer).

750 ng of purified DNA library in 15 µl elution buffer was mixed well with 4 µl blocker mix and incubated in a thermal cycler with the following conditions: (i) 95° C. for 5 minutes; (ii) 65° C. hold. Meanwhile 10 µl of Hybridization Buffer (13×SSPE; 13.5 mM EDTA; 13×Denhart's Solution; 0.45% SDS), 0.5 µl RNase-inhibitor, and 0.5 µl Agilent SureSelect Custom Panel Probe Pool were pre-warmed at 65° C. for 2 minutes. Then the entire contents of the DNA-blocker mix were transferred to the probe mix, allowing the hybridization reaction to proceed at 65° C. for 16-24 hours.

After the hybridization, 25 µl of streptavidin-conjugated DynaBeads™ (Thermo Fisher Scientific, 65602) were conditioned by washing with 200 µl Binding Buffer (10 mM Tris-HCl pH 8.0, 0.5 mM EDTA, 1 M NaCl) for four times. DNA capture was performed at 25° C. in a thermomixer for 30 minutes at 600 RPM. To remove the non-target DNA pulled down via non-specific binding, the beads were first washed once at room temperature with 500 µl of Wash Buffer1 (0.15 M Sodium Chloride, 0.015 M Sodium Citrate, 0.1% SDS), then three times with Wash Buffer2 (0.015 M Sodium Chloride, 0.0015 M Sodium Citrate, 0.1% SDS) at 65° C. The beads were then resuspended in 20 μl of elution buffer (10 mM Tris-HCl, pH 8.0) and used as template for the following indexing PCR step.

Figure 8B:
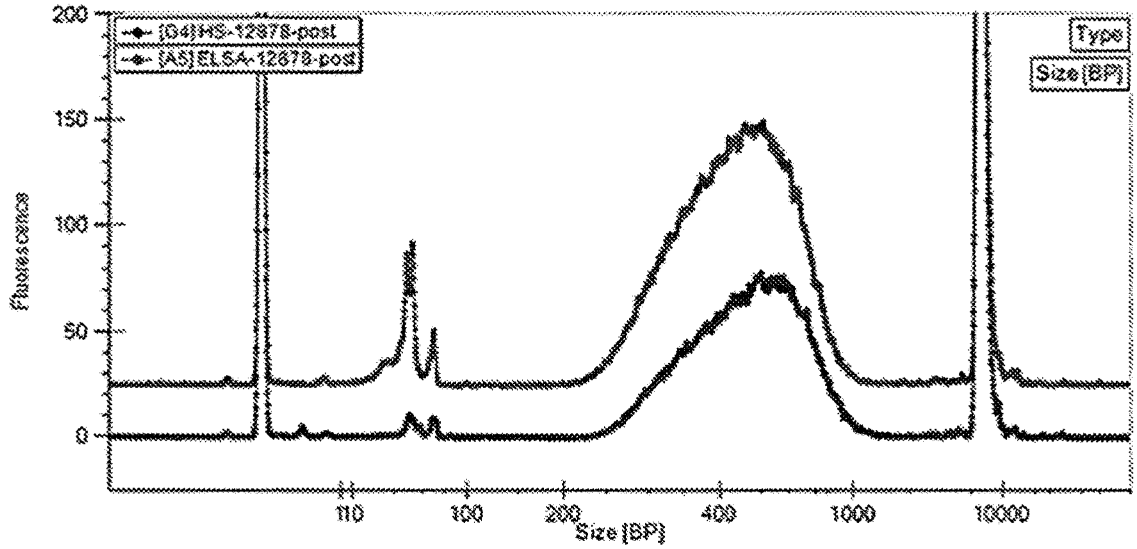

For multiplex sequencing, 5 μl indexing primers (pre-mixed i5 and i7, 20 μM each) were added in a 50 μl reaction containing 20 μl resuspended T1 beads, and 25 μl Kapa HiFi hotstart ready mix (Kapa Biosystem, KK2602). The PCR Program was as follows: (i) 95° C. for 5 minutes; (ii) 98° C. for 20 seconds, 60° C. for 30 seconds, 72° C. for 1 minute, 14 cycles and (iii) 72° C. for 10 minutes. Purified DNA libraries were eluted in 20 μl of EB and quantified by Qubit dsDNA HS assay kit. FIG. 8B illustrates an example plot of a capillary electrophoretic analysis, showing an example size distribution of captured library fragments after Indexing PCR (top and bottom plots are ELSA-12878-post and HS-12878-post, respectively).

The products of the indexing PCR step were sequenced on an Illumina NextSeq using PE150 cycle runs according to the manufacturer's instructions. FASTQ sequences were de-multiplexed by analytical pipeline, and general library quality metrics were analyzed. Illustrative library bioinformatics QC summary tables generated by Picard HSMetrics are shown in Tables 5A-D ("PC1" denotes 0.5% AF DNA mix, "12878" denotes NA12878 genomic DNA).

TABLE 5A

| Sample | Bait Territory | PF Reads | PF Unique Reads | PCT PF UQ Reads | PF UQ Bases Aligned | On Bait Bases |
|---|---|---|---|---|---|---|
| ELSA-12878-1 | 52,552 | 10,904,818 | 6,476,017 | 0.594 | 665,757,553 | 307,386,965 |
| ELSA-12878-2 | 52,552 | 10,769,038 | 6,107,990 | 0.567 | 626,201,560 | 305,050,477 |
| ELSA-PC1-1 | 52,552 | 10,918,648 | 6,254,827 | 0.573 | 635,301,234 | 328,222,731 |
| ELSA-PC1-2 | 52,552 | 10,494,670 | 6,226,391 | 0.593 | 634,757,074 | 316,119,222 |
| HS-12878-1 | 52,552 | 10,184,874 | 3,285,943 | 0.323 | 345,044,568 | 74,843,333 |
| HS-12878-2 | 52,552 | 10,034,950 | 3,258,049 | 0.325 | 341,880,314 | 75,197,794 |
| HS-PC1-1 | 52,552 | 10,293,830 | 3,389,731 | 0.329 | 355,347,808 | 90,862,657 |
| HS-PC1-2 | 52,552 | 9,526,184 | 2,976,248 | 0.312 | 311,924,121 | 70,668,683 |

TABLE 5B

| Sample | Near Bait Bases | Off Bait Bases | On Target Bases | PCT Selected Bases | PCT Off Bait | On Bait vs Selected |
|---|---|---|---|---|---|---|
| ELSA-12878-1 | 73,107,540 | 285,263,048 | 307,386,965 | 0.572 | 0.428 | 0.808 |
| ELSA-12878-2 | 69,640,725 | 251,510,358 | 305,050,477 | 0.598 | 0.402 | 0.814 |
| ELSA-PC1-1 | 66,460,387 | 240,618,116 | 328,222,731 | 0.621 | 0.379 | 0.832 |
| ELSA-PC1-2 | 66,861,856 | 251,775,996 | 316,119,222 | 0.603 | 0.397 | 0.825 |
| HS-12878-1 | 25,087,954 | 245,113,281 | 74,843,333 | 0.29 | 0.71 | 0.749 |
| HS-12878-2 | 24,939,238 | 241,743,282 | 75,197,794 | 0.293 | 0.707 | 0.751 |
| HS-PC1-1 | 26,981,562 | 237,503,589 | 90,862,657 | 0.332 | 0.668 | 0.771 |
| HS-PC1-2 | 21,796,096 | 219,459,342 | 70,668,683 | 0.296 | 0.704 | 0.764 |

TABLE 5C

| Sample | Mean Bait Cover-age | Mean Target Cover-age | PCT Usable Bases On Bait | PCT Usable Bases On Target | Fold Enrich-ment | Zero Cvg Targets PCT |
|---|---|---|---|---|---|---|
| ELSA-12878-1 | 5,849 | 5,849 | 0.255 | 0.255 | 27,252 | 0 |
| ELSA-12878-2 | 5,805 | 5,805 | 0.257 | 0.257 | 28,753 | 0 |
| ELSA-PC1-1 | 6,246 | 6,246 | 0.274 | 0.274 | 30,494 | 0 |
| ELSA-PC1-2 | 6,015 | 6,015 | 0.274 | 0.274 | 29,395 | 0 |
| HS-12878-1 | 1,424 | 1,424 | 0.067 | 0.067 | 12,803 | 0 |
| HS-12878-2 | 1,431 | 1,431 | 0.068 | 0.068 | 12,982 | 0 |
| HS-PC1-1 | 1,729 | 1,729 | 0.08 | 0.08 | 15,092 | 0 |
| HS-PC1-2 | 1,345 | 1,345 | 0.067 | 0.067 | 13,372 | 0 |

TABLE 5D

| Sample | Fold 80 Base Penalty | Hs Library Size | Hs Penalty 50x | Hs Penalty 100x | At Drop-out | GC Drop-out |
|---|---|---|---|---|---|---|
| ELSA-12878-1 | 1.32 | 2,134,279 | 2.88 | 2.89 | 1.03 | 6.07 |
| ELSA-12878-2 | 1.32 | 2,066,386 | 2.72 | 2.73 | 1.06 | 5.6 |
| ELSA-PC1-1 | 1.33 | 2,227,506 | 2.59 | 2.6 | 1.19 | 5.27 |
| ELSA-PC1-2 | 1.33 | 2,191,344 | 2.69 | 2.7 | 1.01 | 5.62 |
| HS-12878-1 | 1.09 | 452,276 | 5.11 | 5.22 | 1.25 | 0.73 |
| HS-12878-2 | 1.09 | 453,694 | 5.06 | 5.16 | 1.29 | 0.71 |
| HS-PC1-1 | 1.1 | 536,676 | 4.35 | 4.43 | 1.46 | 0.62 |
| HS-PC1-2 | 1.09 | 419,039 | 4.93 | 5.03 | 1.64 | 0.57 |

Sequences were analyzed to identify mutations. Somatic mutations called are listed in Tables 6A-C, which compare performance between splinter and "Y" adapter libraries. The splinter adapter libraries had better mutation detection sensitivity in 0.5% AF PC1 but with several putative false positive calls in NA12878.

TABLE 6A

| Mutation | Position | PC1 Expected |
|---|---|---|
| ALK: p.F1174L | 2:29443695, G > T | 0.50% |
| BRAF: p.V600E | 7:140453136, A > T | 0.50% |
| EGFR: p.E746_A750del | 7:55242464, AGGAATTAAGAGAAGC (SEQ ID NO: 21) > A | 0.50% |
| EGFR: p.T790M | 7:55249071, C > T | 0.50% |
| KRAS: p.G12A | 12:25398284, C > G | 0.50% |
| MET: c.3028 + 1G > T | 7:116412044, G > T | 0.50% |
| NRAS: p.Q61H | 1:115256528, T > A | 0.50% |
| PIK3CA: p.E545K | 3:178936091, G > A | 0.50% |
| EGFR: p.G719S | 7:55241707, G > A | 1.00% |
| KRAS: p.G13D | 12:25398281, C > T | 2.00% |
| PIK3CA: p.H1047R | 3:178952085, A > G | 2.00% |
| KRAS: p.G12S | 12:25398285, C > T | |
| MET: c.3028 + 1G > A | 7:116412044, G > A | |
| MET: p.D1010Y | 7:116412043, G > T | |
| MET: p.L238fs | 7:116339847, GT > G | |
| RET: c.2136 + 14C > T | 10:43610198, C > T | |
| Mutation_Count | | |

TABLE 6B

| Mutation | ELSA-12878-1 | ELSA-12878-2 | ELSA-PC1-1 | ELSA-PC1-2 |
|---|---|---|---|---|
| ALK: p.F1174L | | | 0.27% | 0.35% |
| BRAF: p.V600E | | | 0.44% | 0.49% |
| EGFR: p.E746_A750del | | | 0.31% | 0.29% |
| EGFR: p.T790M | | | 0.55% | 0.92% |
| KRAS: p.G12A | | | 0.71% | 0.29% |
| MET: c.3028 + 1G > T | | | 1.49% | 0.65% |
| NRAS: p.Q61H | | | 0.52% | 0.70% |
| PIK3CA: p.E545K | 0.31% | | 0.27% | 0.67% |
| EGFR: p.G719S | | | 1.17% | 0.84% |
| KRAS: p.G13D | | | 2.14% | 1.77% |
| PIK3CA: p.H1047R | | | 2.08% | 1.82% |
| KRAS: p.G12S | | 0.20% | | |

TABLE 6B-continued

| Mutation | ELSA-12878-1 | ELSA-12878-2 | ELSA-PC1-1 | ELSA-PC1-2 |
|---|---|---|---|---|
| MET: c.3028 + 1G > A | | | | 0.17% |
| MET: p.D1010Y | 0.11% | | | |
| MET: p.L238fs | | | 1.76% | 1.69% |
| RET: c.2136 + 14C > T | | | | |
| Mutation Count | 2 | 1 | 12 | 13 |

TABLE 6C

| Mutation | HS-12878-1 | HS-12878-2 | HS-PC1-1 | HS-PC1-2 |
|---|---|---|---|---|
| ALK: p.F1174L | | | 0.64% | 0.64% |
| BRAF: p. V600E | | | 0.71% | 0.55% |
| EGFR: p.E746_A750del | | | 0.17% | 0.14% |
| EGFR: p. T790M | | | 1.12% | 0.44% |
| KRAS: p.G12A | | | 1.26% | 0.60% |
| MET: c.3028 + 1G > T | | | 2.38% | 1.62% |
| NRAS: p.Q61H | | | | 0.18% |
| PIK3CA: p.E545K | | | 0.29% | |
| EGFR: p.G719S | | | 0.63% | 0.95% |
| KRAS: p.G13D | | | 1.94% | 2.16% |
| PIK3CA: p.H1047R | | | 1.89% | 3.12% |
| KRAS: p.G12S | 0.11% | | | |
| MET: c.3028 + 1G > A | | | | 0.76% |
| MET: p.D1010Y | | | | |
| MET: p.L238fs | | | | |
| RET: c.2136 + 14C > T | | | 0.78% | 1.31% |
| Mutation_Count | 1 | 0 | 11 | 12 |

Example 5

Lambda DNA was purchased from Promega (Madison, WI, Catalog number: D1521). The concentration was measured by Qubit dsDNA HS assay kit (Thermo Fisher Scientific, Waltham, MA, Q32851), and the amount of DNA used in library preparation ranged from 1-10 ng. DNA substrates were diluted into 50 μl IDTE buffer (Integrated DNA Technologies, Coralville, IA; Nov. 5, 2001-09), and sheared into fragments of about 100-600 bp using a focused acoustic sonicator (Covaris, Woburn, MA, M220). The sonication parameters were set as follows: peak incident power 50W, duty factor 20%, cycle per burst 200, duration 150 seconds, and temperature 6-8° C. The size of the sheared DNA fragments was confirmed by LabChip GXII touch 24 (Perkin Elmer, Waltham, MA).

The bisulfite conversion step (BC) was carried out with a modified protocol from EZ-96 DNA methylation-lightning™ MagPrep (Zymo, Irvine, CA, D5047). 97.5 μl of Lightning Conversion Reagent and 15 μl of sheared genomic DNA were added in a 48-well Plate (Thermo Fisher Scientific, AB0648). The samples were mixed by pipetting up and down and incubated in a thermal cycler with the following conditions: (i) 98° C. for 8 minutes; (ii) 54° C. for 60 minutes; (iii) 4° C. storage for up to 20 hours. The BC-treated DNA samples were transferred to a 96-well midi-plate (Thermo Scientific, AB0859) with preloaded 450 μl of M-Binding Buffer and 7.5 μl of MagBinding Beads for each well. Components were mixed thoroughly and the plate was allowed to stand at room temperature for 5 minutes. The plate was then transferred to a magnetic stand for an additional 5 minutes, and the supernatant was removed. The beads were washed with 300 μl of M-Wash Buffer and beads were incubated with 150 μl of L-Desulphonation Buffer at room temperature (20-30° C.) for 25 minutes. The plates were placed on the magnetic stand for 3 minutes and supernatant discarded, followed by washing the beads with 300 μl of M-Wash Buffer twice. After the washing step, the plate was transferred to a metal heater (Illumina, San Diego, CA, SC-60-504, BD-60-601) at 55° C. for 30 minutes to dry the beads, then 16 μl of M-Elution Buffer was added with an additional 4 minutes of incubation at 55° C. The plate was then moved to the magnetic stand for 1 minute, and the supernatant was recovered as template for subsequent library prep steps.

Figure 9:
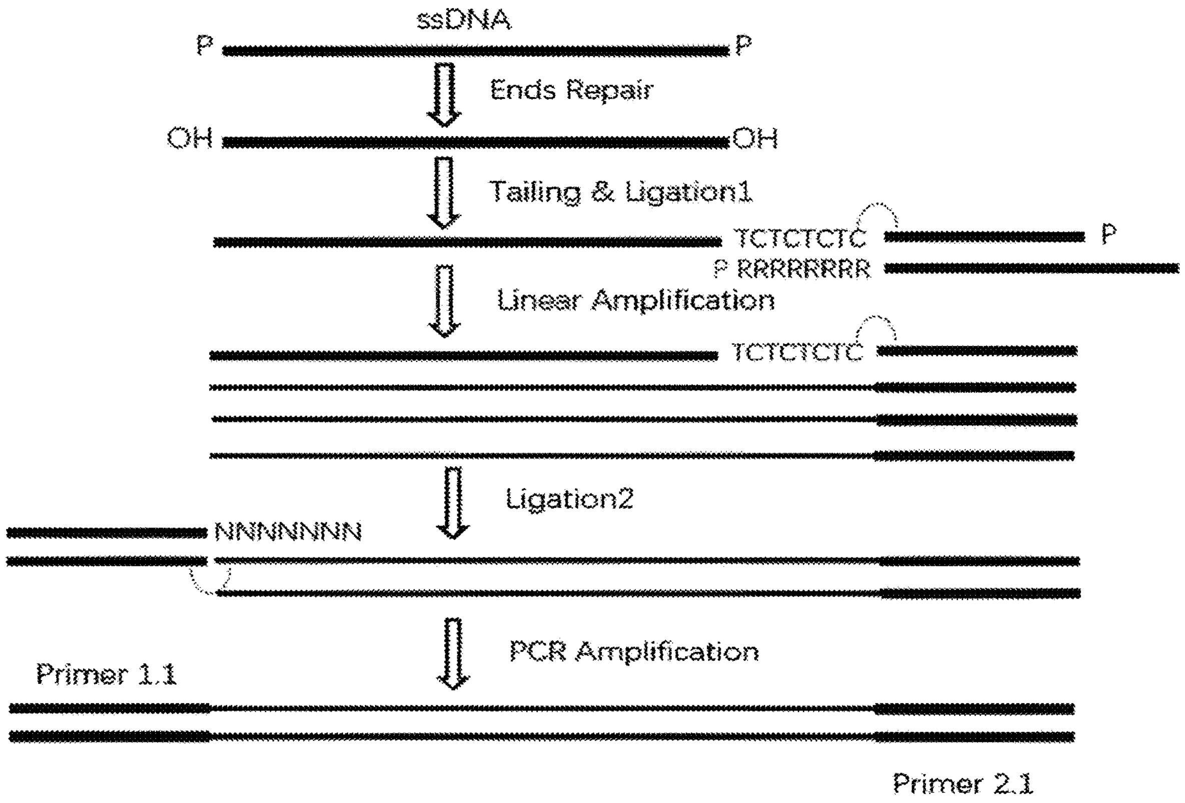
FIG. 9 illustrates an example library preparation method, in accordance with an embodiment of the invention. The illustration includes sequences TCTCTCTC and NNNNNNN, where N is any base.
Figure 10:
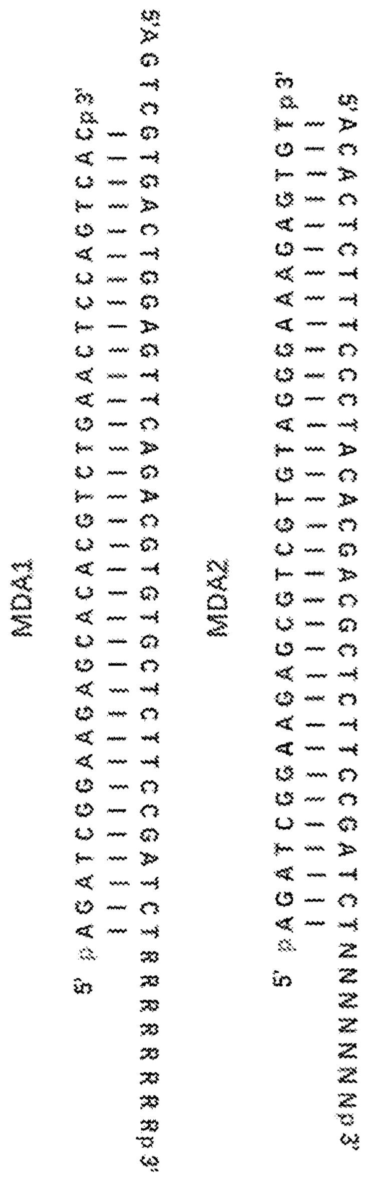
FIG. 10 illustrates example adapters, in accordance with an embodiment of the invention. The illustration includes SEQ ID NOs: 4, 22, 6 and 23, in order from top to bottom.

The adapter MDA1 was designed to have an eight base 3' overhang and a four base 5' overhang on the bottom strand. The 3' overhang has a plurality of eight G or A randomly synthesized at a 3:1 molar ratio. The four base 5' overhang creates a recessive 3' end on the top strand, which prevents leaky TdT activity due to incomplete block of the 3' end of the top strand. During the first tailing and ligation step, the 3' overhang annealed to the 3' end poly-C/T tail of the single stranded DNA substrate (as illustrated in FIG. 9). The sequences of the oligonucleotides forming MDA1 are illustrated in FIG. 10. The MDA1 adapter was prepared by annealing oligo ATN-R2-Top and ATN-R2-Bot together. In detail, 50 μl of each oligo (100 μM) was mixed and incubated at 95° C. for 10 minutes and allowed to slowly cool to room temperature in 10 mM Tris-HCl containing 0.1 mM EDTA and 50 mM NaCl. The 3' ends of both oligos were blocked by a phosphate group to prevent self-ligation.

The MDA2 adapter was designed to have a plurality of seven N (A, T, G or C randomly synthesized at 1:1:1:1 molar ratio). It annealed to the 3' end of the single stranded DNA substrate and prompted the ligation between MDA2 and DNA substrate during the second ligation step (as illustrated in FIG. 9). The MDA2 adapter was prepared by annealing oligo ATN-R1-Top and ATN-R1-Bot together. The sequences of the oligonucleotides forming MDA2 are illustrated in FIG. 10. Sequences for oligonucleotides forming MDA1, MDA2, and for an amplification primer designated "Anchor primer" are set forth in Table 7.

TABLE 7

| Oligo | Sequence | Notes |
|---|---|---|
| ATN-R2-Top | AGATCGGAAGAGCACACGTCTGAAC TCCAGTCAC (SEQ ID NO: 4) | 5' phosphate; 3' phosphate |
| ATN-R2-Bot | AGTCGTGACTGGAGTTCAGACGTGT GCTCTTCCGATCTRRRRRRRR (SEQ ID NO: 22) | 3' phosphate; R (G:A) = 3:1 premix |
| ATN-R1-Top | AGATCGGAAGAGCGTCGTGTAGGGA AAGAGTGT (SEQ ID NO: 6) | 5' phosphate; 3' phosphate |
| ATN-R1-Bot | ACACTCTTTCCCTACACGACGCTCTT CCGATC (SEQ ID NO: 23) | 3' phosphate |
| LAP (Anchor primer) | GTGACTGGAGTTCAGACGTGTGCTCT TCCGATC (SEQ ID NO: 16) | |

Bisulfite converted DNA fragments were end-repaired by mixing 12.5 μl of DNA sample, 1.5 μl of 10× CutSmart buffer (NEB, B7204S), 1 μl Shrimp alkaline phosphatase (New England Biolabs (NEB), Ipswich, MA, M0371L), and incubated at 37° C. for 30 minutes. The products were further denatured by incubating at 95° C. for 5 minutes and fast cooling on ice.

Next, the first ligation reaction was performed in a 20 μl reaction volume containing pretreated DNA substrates, 1×CutSmart Buffer, 0.25 mM $CoCl_2$ (NEB, B0252S), 0.025 mM β-Nicotinamide adenine dinucleotide (NEB, B9007S), 0.09 mM dCTP (Roche, 11934520001, sold by Sigma-Aldrich, St. Louis, MO), 0.01 mM dTTP (Roche, 11934546001, 1 μM MDA1 adapter, 0.5 U/μl *E. coli* ligase (NEB, M0205L) and 0.5 U/μl terminal deoxynucleotidyl transferase (TdT, NEB, M0315S). The reaction was incubated at 37° C. for 30 minutes followed by heating at 95° C. for 2 minutes and held at 4° C.

The ligated product was extended and linearly amplified in the presence of 1X KAPA HiFi HotStart Uracil+ReadyMix (KAPA Biosystems, Wilmington, MA, KK2802), and 0.91 μM anchor primer. The linear amplification reaction was carried out with the following thermal profile: (i) 95° C. for 5 minutes; (ii) 98° C. for 20 seconds, 62° C. for 30 seconds, 72° C. for 1 minute, 15 cycles and (iii) 72° C. for 5 minutes. After the reaction was completed, buffer was exchanged by purification with 2.5X AMPure XP beads (Beckman Coulter, Brea, CA, A63881) and eluted with 11.5 μl Elution Buffer (EB) (10 mM Tris-HCl, pH 8.0).

The second ligation reaction was performed in a 20 μl reaction volume containing 10 μl of purified DNA products, 1X T4 DNA ligase buffer, 10% PEG8000, 1 μM MDA1 adapter and 20 U/μl T4 DNA ligase (NEB, M0202L). The reaction was incubated at 20° C. for 30 minutes followed by heating at 65° C. for 20 minutes and held at 4° C.

PCR enrichment of ligated product was performed in a 50 μl reaction containing 20 μl of the above-mentioned DNA product, 1X KAPA HiFi buffer, dNTP, 1 μM primer F and primer R, and 1 U/μl KAPA HiFi polymerase. The PCR program was as follows: (i) 95° C. for 5 minutes; (ii) 98° C. for 20 seconds, 60° C. for 30 seconds, 72° C. for 1 minute, 8 cycles and (iii) 72° C. for 10 minutes. The PCR products were purified using Agencourt AMPure XP beads (Beckman Coulter, A63881) and eluted in 18 μl of EB (10 mM Tris-HCl, pH 8.0).

For multiplex sequencing, 5 μl indexing primers (premixed i5 and i7, 20 μM each) were added in a 50 μl reaction containing 1 μl of the above purified PCR product, and 25 μl Kapa HiFi hot start ready mix (Kapa Biosystem, KK2602). The PCR Program was as follows: (i) 98° C. for 45 seconds; (ii) 98° C. for 15 seconds, 60° C. for 30 seconds, 72° C. for 1 minute, 6 cycles and (iii) 72° C. for 5 minutes. Purified DNA libraries were eluted in 20 μl of EB and quantified by Qubit dsDNA HS assay kit.

Figure 11:
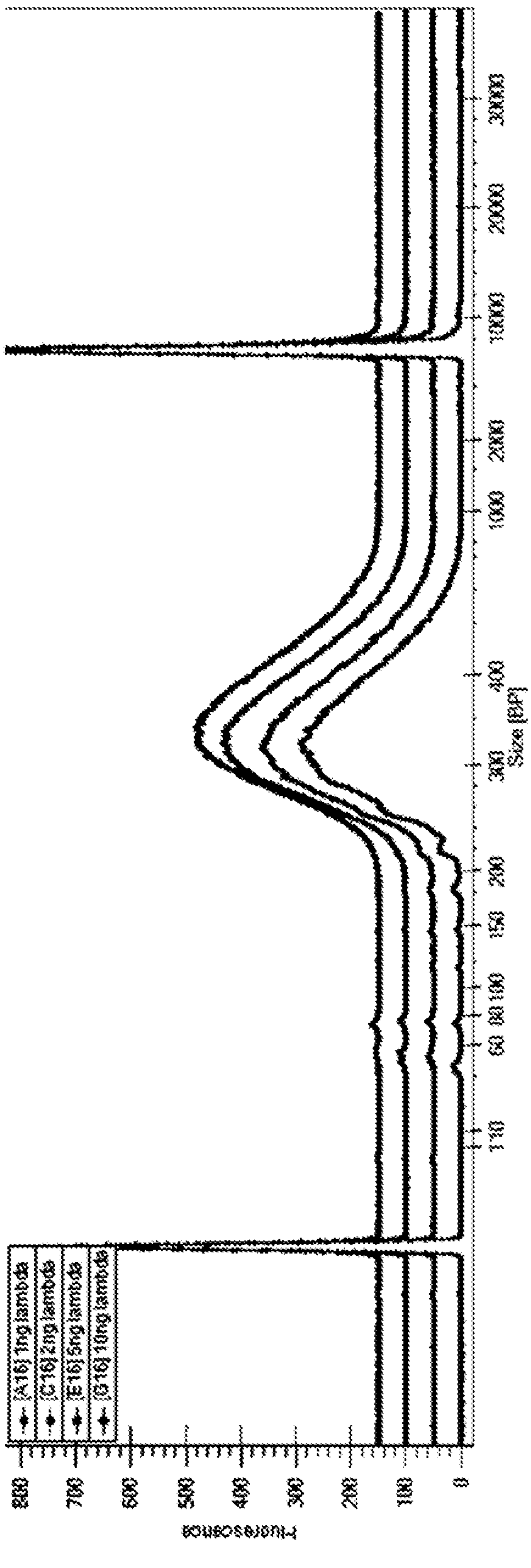
FIG. 11 illustrates an example plot of a capillary electrophoretic analysis (lines on graph from top to bottom, 10 ng lambda, 5 ng lambda, 2 ng lambda, 1 ng lambda).

FIG. 11 illustrates an example plot of a capillary electrophoretic analysis, showing size distribution of library fragments after indexing PCR. All libraries were loaded on HT DNA High Sensitivity LabChip Kit (Perkin Elmer).

The products of the indexing PCR step were sequenced on an Illumina Novaseq using PE150 cycle runs according to the manufacturer's instructions. FASTQ sequences were de-multiplexed by analytical pipeline, and general library quality metrics were analyzed. Illustrative library bioinformatics QC summary table istables are shown in Tables 8 below.

TABLE 8A

| Sample Name | Specimen | Input DNA (ng) | Total PF Reads | Mapped Ratio | Insert Size |
|---|---|---|---|---|---|
| 1 ng-lambda | lambda genomic DNA | 1 | 1575300 | 0.988 | 157 |
| 2 ng-lambda | lambda genomic DNA | 2 | 1262550 | 0.989 | 158 |
| 5 ng-lambda | lambda genomic DNA | 5 | 1276862 | 0.991 | 161 |
| 10 ng-lambda | lambda genomic DNA | 10 | 1448128 | 0.992 | 168 |

TABLE 8B

| Sample Name | Deduped Median Coverage | Pre-deduped median Coverage | fold.80.base.penalty |
|---|---|---|---|
| 1ng-lambda | 3505 | 4160 | 1.11 |
| 2ng-lambda | 2904 | 3353 | 1.11 |
| 5ng-lambda | 2965 | 3430 | 1.12 |
| 10ng-lambda | 3377 | 3954 | 1.11 |

An overview illustration of the library preparation method described above is provided in FIG. 9. A tailing step is performed using TdT with appropriate dNTP(s) to create a homopolymer or near-homopolymer tail to the 3' end of ssDNA fragments. The homopolymer anneals to the 3' overhang of an adapter containing a 5' phosphate group in the top strand. The ligation reaction catalyzed by ligase seals the 3' end of the ssDNA fragment to prevent excessive tailing. The bottom strand of the adapter is competed out by the anchor primer, exposing the initiating sites for a linear amplification process. The amplified ssDNA strands serve as substrate for the second round of ligation, where splint oligonucleotides were used to create short stretches of dsDNA fragments that allow subsequent ligation of adapters using standard dsDNA ligation with T4 DNA ligase.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entireties.

What is claimed is:

1. A method for preparing a polynucleotide library, the method comprising, in the following order:

(a) in a first tailing reaction, adding a first tail to each of a plurality of target polynucleotides by template-independent polymerization of a pool of nucleotides consisting of dCTP and dTTP, wherein the dCTP and the dTTP are in a ratio selected from the group consisting of 9:1 and 3:1, such that the first tail has a ratio of dCTP to dTTP selected from the group consisting of 9:1 and 3:1, and the first tail is a single-stranded polynucleotide, wherein each of the plurality of target polynucleotides comprises a single-stranded polynucleotide, wherein the first tailing reaction further comprises hybridizing a first adapter to the first tail, wherein the first adapter comprises a first strand and a second strand forming a double-stranded region and an overhang within the first strand of the first adapter, and wherein the overhang of the first adapter is hybridized to the first tail;

(b) in a first ligation reaction, ligating one end of the second strand of the first adapter that is on the same side of the overhang in the first adaptor to the end of the first tail;

(c) in a linear amplification reaction, hybridizing a first primer to the second strand of the first adaptor that is ligated to the first tail in (b) and extending the first primer, and repeating the hybridizing and extending for a total of 10 to 15 cycles to linearly amplify each of the plurality of target polynucleotides, thereby producing a plurality of complement target polynucleotides; and (d) in a second ligation reaction, ligating a strand of a second adapter to the plurality of complement target polynucleotides at the end opposite to the first primer.

2. The method of claim 1, wherein (d) comprises (d-1) and (d-2) in the following order, (d-1) in a second tailing reaction, wherein a second tail is added to each of the plurality of complement target polynucleotides, which are the linear amplification products complementary to the first tail of the plurality of target polynucleotides by template-independent polymerization, wherein the second tail can have a different sequence from the first tail, depending upon the one or more nucleotides in the nucleotide pool for the second tailing reaction, wherein the second tail is a single-stranded polynucleotide, wherein the second tailing reaction further comprises hybridizing the second adapter to the second tail, wherein the second adapter comprises a first strand and a second strand forming a double-stranded region and an overhang within the first strand of the second adapter, wherein the overhang of the second adapter is hybridized to the second tail; and (d-2) in the second ligation reaction, ligating the second strand of the second adapter to the second tail.

3. The method of claim 1, wherein the method further comprises: (i) directly hybridizing the second adapter to each of the plurality of complement target polynucleotides, wherein the second adapter comprising a first strand and a second strand forming a double-stranded region and an overhang within the first strand of the second adapter, wherein the overhang of the second adapter is hybridized to each of the plurality of complement target polynucleotides, and (ii) directly ligating the second strand of the second adapter to the plurality of complement target polynucleotides.

4. The method of claim 1, wherein the method further comprises prior to (a) of claim 1, one or more of: (i) fragmenting polynucleotides to produce the target polynucleotides; (ii) dephosphorylation of one or both ends of the target polynucleotides; and (iii) denaturing double-stranded polynucleotides to single-stranded polynucleotides to produce each of the plurality of target polynucleotides.

5. The method of claim 4, further comprising prior to (ii) of claim 4 differentially modifying methylated cytosines or unmethylated cytosines in each of the plurality of target polynucleotides, wherein differentially modifying methylated cytosines or unmethylated cytosines comprises treating each of the plurality of target polynucleotides with bisulfite.

6. The method of claim 2, wherein the nucleotide pool for the second tailing reaction consists of one or two types of nucleotides, wherein the one or two types of nucleotides contains or respectively contain DNA bases selected from the group consisting of adenine (A), thymine (T), guanine (G) and cytosine (C).

7. The method of claim 2, wherein (i) the first adapter and the second adapter comprise double-stranded regions that are different in polynucleotide sequences, or (ii) the overhang within the first strand of the first adapter or the overhang within the first strand of the second adapter is a 3'-overhang.

8. The method of claim 7, wherein the first adapter or the second adapter further comprises a 5'-overhang.

9. The method of claim 2, further comprising amplifying the plurality of complement target polynucleotides by extending a second primer hybridized to the second strand of the second adapter that is ligated to the second tail in (d-2) of claim 2.

10. The method of claim 9, further comprising an exponential amplification reaction with a third primer and a fourth primer, wherein (i) the third primer hybridizes to a complement of at least a portion of the first primer, and (ii) the fourth primer hybridizes to a complement of at least a portion of the second primer.

11. The method of claim 10, wherein the third primer, the fourth primer, or both the third primer and the fourth primer comprise an index sequence that identifies a sample source of each of the plurality of target polynucleotides.

12. The method of claim 11, further comprising:

(e) sequencing the exponential amplification products of the exponential amplification reaction comprising the third primer and the fourth primer; and (f) grouping sequencing reads according to the index sequence.

13. The method of claim 12, wherein sequencing comprises detecting a sequence variant in one or more of the plurality of target polynucleotides or a difference in nucleotide methylation in one or more of the plurality of target polynucleotides, relative to a reference sequence.

14. The method of claim 2, wherein the overhang within the first strand of the first adapter consists of nucleotides (G) and (A) in a ratio selected from a group consisting of 9:1 and 3:1.

* * * * *